United States Patent [19]
Schramm et al.

[11] Patent Number: 6,121,296
[45] Date of Patent: Sep. 19, 2000

[54] TRANSITION-STATE INHIBITORS FOR NUCLEOSIDE HYDROLASE AND TRANSFERASE REACTIONS

[75] Inventors: Vern L. Schramm, New Rochelle, N.Y.; Benjamin Horenstein, Gainesville, Fla.

[73] Assignee: Albert Einstein College of Medicine of Yeshiva University, Bronx, N.Y.

[21] Appl. No.: 09/017,097

[22] Filed: Feb. 2, 1998

Related U.S. Application Data

[63] Continuation-in-part of application No. 08/781,745, Jan. 10, 1997, abandoned, which is a continuation of application No. 08/427,730, Apr. 24, 1995, abandoned, which is a continuation of application No. 07/971,871, Nov. 4, 1992, abandoned.

[51] Int. Cl.⁷ .......................... A61K 31/40; C07D 207/08
[52] U.S. Cl. ............................. 514/343; 514/81; 514/89; 514/94; 514/256; 514/258; 514/397; 514/424; 514/425; 424/157.1; 424/158.1; 424/169.1; 424/170.1; 424/236.1; 424/241.1; 424/257.1; 424/260.1; 424/265.1; 544/235; 544/243; 544/244; 544/262; 544/335; 546/22; 546/278.4; 546/278.7; 548/314.7; 548/413
[58] Field of Search ................................. 548/556, 314.7, 548/413; 514/424, 425, 343, 256, 258, 397, 81, 89, 94; 546/278.4, 278.7, 22; 544/335, 262, 243, 244; 424/157.1, 158.1, 169.1, 170.1, 236.1, 241.1, 257.1, 260.1, 265.1

[56] References Cited

U.S. PATENT DOCUMENTS

| | | |
|---|---|---|
| 2,878,264 | 3/1959 | Lunsford . |
| 5,041,555 | 8/1991 | Fleet et al. . |
| 5,089,520 | 2/1992 | Fleet et al. ............................. 514/425 |
| 5,098,927 | 3/1992 | Takatsuki et al. ...................... 514/425 |

FOREIGN PATENT DOCUMENTS

| | | |
|---|---|---|
| 2143539 | 2/1973 | France . |

OTHER PUBLICATIONS

"Enzyme–Catalyzed Aldol Condensation for Asymmetric Synthesis of Azasugars: Synthesis, Evaluation, and Modeling of Glycosidase Inhibitors" by Kajimoto, in *J. Am. Chem. Soc.*, vol. 113, pp. 6187–6196 (1991).

"Amino–SubstituTed–β–Benzyl–C–Glycosides; Novel β–Glycosidase Inhibitors" by Schmidt et al., in *Angew. Chem. Int. Ed. Engl.*, vol. 30, pp. 1328–1329 (1991).

"Enzyme–Catalyzed Synthesis of 1–Deoxymannojirimycin, 1–Deoxynojirimycin, and 1,4–Dideoxy–1,4–Imino–D–Arabinitol" by Ziegler et al., in *Angew. Chem. Int. Ed. engl.*, Vol. 27, No.5, pp. 716–717 (1988).

"Potent Competitive Inhibition of α–Galactosidase and αGlucosidase Activity by 1,4–Dideoxy–1,4–Iminopenti-Tols: Syntheses of 1,4–Dideoxy–1,4–Imino–D–Lyxitol and of Both Enantiomers of 1,4–Dideoxy–1,4–Iminoarabinitol" by Fleet et al., in *Tetrahedron Letters*, vol. 26, No. 26, pp. 3127–3130 (1995).

Parkin, et al., Nucleoside Hydrolase from *Crithidia fasciculata*, J. Biol. Chem., 1991, 266(31), 20658–20665.

Horenstein, et al., Transition State Analysis of Nucleoside Hydrolase from *Crithidia fasciculata*, Biochemistry, 1991, 30(44), 10788–10795.

Kline and Schramm, Purine Nucleoside Phosphorylase. Ionine Hydrolysis, Tight Binding of the Hypoxanthine Intermediate, and Third–the–Sites Reactivity, Biochemistry, 1992, 31, 5964–5973.

Horenstein and Schramm, Electronic Nature of the Transition State for Nucleoside Hydrolase. A Blueprint for Inhibitor Design, Biochemistry, 1993, 32, 7089–7097.

Horenstein and Schramm, Correlation of the Molecular Electrostatic Potential Surface of an Enzymatic Transition State with Novel Transition–State Inhibitors, Biochemistry, 1993, 32, 9917–9925.

Boutellier, et al., Amidrazone Analogues of D–Ribofuranose as Transition–State Inhibitors of Nucleoside Hydrolase, Biolchemistry, 1994, 33, 3994–4000.

Schramm, et al., Transition State Analysis and Inhibitor Design for Enzymatic Reactions, Journal of Biological Chemistry, 1994, 269(28), 18259–18262.

Estupinan and Schramm, Guanosine–Inosine–Preferring Nucleoside N–Glycohydrolase from *Crithidia fasciculata*, Journal of Biological Chemistry, 1994, 269(37) 23068–23073.

Kline and Schramm, Pre–Steady–State Transition–State Analysis of the Hydrolytic Reaction Catalyzed by Purine Nucleoside Phosphorylase, Biolchemistry, 1995, 34, 1153–1162.

Parkin and Schramm, Binding Modes for Substrate and a Proposed Transition–State Analogue of Protozoan Nucleoside Hydrolase, Biochemistry, 1995, 34, 13961–13966.

Degano, et al., Three–Dimensional Structure of the Inosine–Uridine Nucleoside N–Ribohydrolase from *Crithidia fasciculata*, Biochemistry, 1996, 35, 5971–5981.

Chen, et al., Inhibition of Ricin by an RNA Stem–Loop Containing a Ribo–Oxocarbenium Mimic, Journal of the American Chemical Society, 1996, 118, 3067–3068.

Parkin et al., Isozyme–Specific Transition State inhibitors for the Trypanosomal Nucleoside Hydrolases, Biochemistry, 1997, 36, 3528–3534.

Furneaux, et al., Synthesis of Transition State Inhibitors for N–Riboside Hydrolases and Transferases, 1997, 53(8); 2915–2930.

*Primary Examiner*—Joseph McKane
*Attorney, Agent, or Firm*—Amster, Rothstein & Ebenstein

[57] ABSTRACT

This invention is directed to transition-state analog compounds and to the use of said compounds as inhibitors of nucleoside hydrolase and transferase enzyme activity of parasites. This invention is further directed to the use of said compounds to treat infections and diseases caused by certain bacterial and plant toxins.

22 Claims, 12 Drawing Sheets

1 2 3 4 5 6 7 8

Key Reactant State Bond Lengths

| Bond | Length, Å | Bond | Length, Å |
| --- | --- | --- | --- |
| C1'-N9 | 1.477 | C2'-H2' | 1.128 |
| C1'-O4' | 1.417 | N9-C8 | 1.372 |
| C1'-C2' | 1.530 | C8-N7 | 1.308 |
| C1'-H1' | 1.128 | | |

Transition State Bond Lengths

| BOND | Bond Length |
|---|---|
| C1'−N9 | 1.97 ± 0.14 Å |
| C1'−O' | 3.0 ± 0.4 Å |
| O4'−C1' | 1.30 ± 0.05 Å |
| C2'−H2' | 1.160 ± 0.001 Å |
| C1'−C2' | 1.502 ± 0.001 Å |
| N7−C8 | 1.346 ± 0.006 Å |
| C8−N9 | 1.332 ± 0.006 Å |

Reagents: i, (Boc)₂O, CH₂Cl₂, Et₃N; ii, (Ph₃P)₃RhCl, aq CH₃CN; iii, oxone, aq acetone.

SCHEME 2

TRANSITION-STATE INHIBITORS FOR NUCLEOSIDE HYDROLASE AND TRANSFERASE REACTIONS

CROSS REFERENCE TO RELATED APPLICATIONS

This application is a continuation-in-part of U.S. application Ser. No. 08/781,745, filed Jan. 10, 1997 now abandoned, which is a file wrapper continuation of U.S. application Ser. No. 08/427,730, filed Apr. 24, 1995, now abandoned, which is a continuation of U.S. application Ser. No. 07/971,871, filed Nov. 4, 1992 now abandoned, the contents of each of which are hereby incorporated by reference in their entirety.

STATEMENT OF GOVERNMENT INTEREST

This invention was made with government support under NIH Grant No. GM41916. The government has certain rights in this invention.

FIELD OF THE INVENTION

This invention is directed to transition-state analog compounds and to the use of said compounds to inhibit the biochemical activity of nucleoside hydrolase and transferase enzymes found in parasitic organisms, such as protozoa and helminths. The transition-state analog compounds of this invention are also effective agents against certain bacterial and plant toxins.

BACKGROUND OF THE INVENTION

Enzymes are naturally-occurring proteins in the body that speed up the rate of biological reactions in the body without themselves being used up in the reactions. As such, enzymes serve as catalysts for biochemical reactions. Nucleosides are compounds consisting of a nitrogen-containing base (e.g., a purine or pyrimidine) linked to a sugar. Nucleoside hydrolases are enzymes in parasitic organisms, such as protozoa and helminth parasites, which catalyze the hydrolysis of purine and pyrimidine nucleosides. Typically, the nucleoside hydrolase enzymes permit parasitic organisms to salvage purines from the blood of hosts. Adenosine ribosyltransferases are enzymes derived from bacterial toxins which cause physiological damage in cholera, diphtheria and pertussis infections.

Many parasites depend on nucleoside hydrolase and transferase activity for purine salvage. Byway of example, *Crithidia fasciculata* is a trypanosome parasite of the mosquito which does not infect mammals. It is dependent on purine salvage and provides a convenient biological system for understanding the enzymology of purine salvage in trypanosomes. It has been reported that Crithidia, as well as pathogenic trypanosomes such as *Trypanosoma cruzi*, contain nucleoside hydrolase enzymes which cleave the N-glycosidic bond of purine and pyrimidine ribosides. *Crithidia luciliae* is another trypanosome parasite which is dependent on purine salvage and also provides a biological system for understanding the enzymology of purine salvage.

Purine salvage is necessary for most or all protozoan and helminth parasites. Protozoan parasites include Entamoeba, a cause of dysentary, Giardia, the cause of giardiasis, Trichomonas, the cause of a vaginitis, Leischmania, the cause of leichmaniasis, Trypanosoma, which causes Chagas disease and sleeping sickness, Balantidium, which causes dysentary and Plasmodium, which causes malaria. Helminth parasites include tapeworms, schistosomes, filariae worms, cestodes, nematodes and trematodes. These parasites cause schistomiasis, hookworm, filariae disease, onchocerciosis, loiasis, pinworm, tapeworm and roundworm infections.

In addition, when bacterial cells infect a host, the bacteria release poisons harmful to body tissues. Such poisons are generally referred to as toxins. By way of example, ADP-ribosylation toxins are common in bacterial infections. The toxins use NAD+ and transfer ADP-ribose to regulate guanine nucleotide binding proteins to disrupt cellular function. These toxins include *E. coli* enterotoxin, Pseudomonas enterotoxin, cholera toxin, diphtheria toxin, tetanine toxin, botulinum toxin and pertussis toxin as well as other bacterial toxins. Ricin is an example of a plant toxin used in cancer chemotherapy. In the body, toxins can act as antigens, and special antibodies, commonly referred to as anti-toxins, may be formed to neutralize the effects of the toxins in individuals who have been infected or previously immunized. In order to treat individuals who have not been immunized or previously infected, it is desirable to produce compounds which are able to act directly against bacterial toxins.

Because of the infections and diseases which are caused by the salvage of purines and pyrimidines by parasitic organisms from the blood of their hosts, a need exists to develop a method of preventing purine and pyrimidine salvage by parasitic organisms. Since purine and pyrimidine salvage is performed by nucleoside hydrolase and transferase enzymes, it is desirable to inhibit the nucleoside hydrolase and transferase enzyme activity of parasitic organisms, thereby preventing and treating infections and diseases caused by parasitic organisms.

U.S. Pat. No. 5,098,927 ("the '927 Patent"), issued to Takatsuki et al. dated Mar. 24, 1992 entitled "Antiretroviral Agent, Method Of Use Thereas, and Method of Preparation", is directed to pyrroline compounds which are effective in the treatment of retroviral infection and lymphadenopathy. The compounds of the '927 Patent are 5-membered rings containing 4 carbons and 1 nitrogen. However, these compounds are effective on lymphatrophic retroviruses, and are ineffective against nucleoside hydrolase and transferase activity.

U.S. Pat. No. 5,089,520 ("the '520 Patent") issued to Fleet et al. on Feb. 18, 1992, entitled "Method of Inhibiting Virus", is directed to 5- and 6-membered compounds having a nitrogen and 2 to 3 hydroxyl substituents on the rings. The compounds of the '520 Patent are described as effective inhibitory agents of human immunodeficiency virus, but are not effective on nucleoside hydrolase or transferase enzyme activity, and therefore are not effective agents against purine and pyrimidine salvage, or toxins.

The article entitled "Potent Competitive Inhibition of a-Galactosidase and a-Glucosidase Activity by 1,4-Dideoxy-1,4-Iminopentitols: Syntheses of 1,4-Dideoxy-1,4-Imino-D-Lyxitol and of Both Enantiomers of 1,4-Dideoxy-1,4-Iminoarabinitol", by Fleet et al., in *Tetrahedron Letters*, Vol.26, No. 26, pages 3127–3130 (1985) is directed to the synthesis of compounds comprising 5-membered carbon rings containing a nitrogen. The compounds synthesized by Fleet et al. act as inhibitors of a-galactosidase, a-glucosidase and glycosidase activity. However, these compounds are not effective against nucleoside hydrolase and transferase enzyme activity.

The article entitled "Enzyme-Catalyzed Aldol Condensation for Asymmetric Synthesis of Azasugars: Synthesis, Evaluation, and Modeling of Glycosidase Inhibitors", by Kajimoto et al., in *J. Am. Chem. Soc.*, Vol. 113, pages 6187–6196 (1991) is directed to the synthesis of compounds which are effective inhibitors of glycosidase activity. The compounds synthesized by Kajimoto et al. are not effective agents against nucleoside hydrolase or transferase enzyme activity, and hence, are not effective in the prevention of purine or pyrimidine salvage.

The article entitled "Amino-Substituted β-Benzyl-C-glycosides; Novel β-Glycosidase Inhibitors", by Schmidt et al., in *Angew. Chem. Int. Ed. Engl.* Vol. 30, pages 1328–1329 (1991) discussed the synthesis of compounds which act as β-glycosidase inhibitors. Again, these compounds have no inhibitory effect on nucleoside hydrolase or transferase enzyme activity.

The article entitled "Enzyme-Catalyzed Synthesis of 1-Deoxymannojirimycin, 1-Deoxynojirimycin, and 1,4-Dideoxy-1,4-imino-D-arabinitol", by Ziegler et al., is directed to the production of 5-membered carbon rings containing nitrogen. The compounds discussed therein are effective glycosidase inhibitors. These compounds are ineffective inhibitors of nucleoside hydrolase and transferase enzyme activity, and hence, are ineffective agents against purine and pyrimidine salvage, and toxins.

Because no compounds have been developed to date which are capable of inhibiting nucleoside hydrolase and transferase enzyme activity of parasitic organisms, thereby preventing the salvage of purines and pyrimidines from the blood of hosts, the infections and diseases caused by purine and pyrimidine salvage by parasites remain problematic. Hence, it is desirable to develop compounds capable of inhibiting nucleoside hydrolase and transferase enzyme activity.

It is therefore an object of this invention to provide compounds capable of inhibiting the biochemical activity of nucleoside hydrolase and transferase enzymes in parasites.

It is another object of this invention to provide a method of inhibiting nucleoside hydrolase and transferase activity.

It is a further object of this invention to provide a method of treating parasitic infections and diseases which involve nucleoside hydrolase and transferase enzyme activity.

It is still another object of this invention to provide compounds which are effective against certain bacterial toxins.

It is a still further object of this invention to provide a method of treating infections caused by bacteria and bacterial toxins.

It is a further object of this invention to provide a method of inhibiting toxins which are used in cancer chemotherapy.

BRIEF DESCRIPTION OF THE DRAWINGS

The above brief description, as well as further objects and features of the present invention, will be more fully understood by reference to the following detailed description of the presently preferred, albeit illustrative, embodiments of the present invention when taken in conjunction with the accompanying drawing wherein.

SUMMARY OF THE INVENTION

Figure 1:
FIG. 1 represents a polyacrylamide gel electrophoresis of nucleoside hydrolase in sodium dodecyl sulfate. Lane 1 shows a sample following DEAE chromatography. Lane 2 and 3 show 10 and 10 mg of protein following Red A chromatography steps. Lanes 4 and 8 show molecular weight standards. Lanes 5, 6 and 7 show 0.6, 6 and 61 mg of nucleoside hydrolase following purification by Superdex 200 gel-exclusion chromatography.

This invention relates to transition-state analog compounds of nucleoside hydrolase and to the use of said compounds as inhibitors of nucleoside hydrolase and transferase enzyme activity. Nucleoside hydrolase and transferase enzymes are found in parasitic organisms, such as protozoa and helminths. The compounds of this invention also act against certain bacterial toxins. The compounds of this invention serve as antibiotics, binding to the nucleoside hydrolase and transferase target enzymes of parasites, thereby inhibiting the activity of said enzymes. By inhibiting the activity of said enzymes, the parasites become unable to salvage purines and pyrimidines from the blood of their hosts.

The transition-state analog inhibitor compounds of this invention are pentose analogs which contain 5-membered rings. They contain 5 carbon atoms and 1 nitrogen atom, with a hydroxyl at carbon 3. Substituents at carbons 1, 2, and 5 and/or the nitrogen complete the structure. The compounds are tailored to resemble the transition-states of nucleoside hydrolase and transferase enzymes. The compounds of this invention resemble the ribose configuration in that there are pentose sugars with 5 carbon atoms. The compositions of this invention are analogs of the transition-state of nucleosidases, and have a charge distribution substantially similar to the charge distribution of the transition-state catalyzed by nucleosidases. Said compounds contain a positive charge. The compounds of this invention are represented by the following formula:

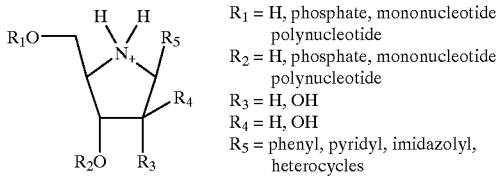

$R_1$ = H, phosphate, mononucleotide polynucleotide
$R_2$ = H, phosphate, mononucleotide polynucleotide
$R_3$ = H, OH
$R_4$ = H, OH
$R_5$ = phenyl, pyridyl, imidazolyl, heterocycles The compounds of this invention can be administered to treat infections and diseases involving nucleoside hydrolase and transferase enzyme activity, which activity includes the salvage of purines and pyrimidines by parasitic organisms from the blood of hosts. The compounds of this invention can also be administered so as to neutralize certain bacterial toxins. Administration may be performed in any acceptable manner, including oral administration and administration by injection.

The compounds of this invention may also be used to treat a composition to inactivate a parasite or toxin. Non-limiting examples of compositions include blood, blood derivatives, plasma, water and milk.

DETAILED DESCRIPTION OF THE INVENTION

This invention is directed to transition-state analog compounds. The compounds of this invention contain 5-membered carbon rings which contain 4 carbon atoms and 1 nitrogen atom, with a hydroxyl at carbon 3. In a preferred embodiment of this invention, there is a hydroxymethyl group at carbon 4. Various substituents may be used at carbons 1, 2 and 5, and/or the nitrogen. The compounds of this invention resemble the transition-states of nucleoside hydrolase and transferase enzymes, and have a charge distribution substantially similar to the charge distribution of the transition-state catalyzed by nucleoside hydrolase. Further, the compounds of this invention contain a positive charge.

The compounds of this invention mimic the oxycarbonium nature of the transition state for nucleoside hydrolase (ribosyl-N-glycohydrolases) and inhibit the activity of nucleoside hydrolases, deoxynucleoside hydrolases, ADP-ribosyltransferases and RNA and DNA N-glycohydrolases.

The compounds of this invention are represented by the following formula:

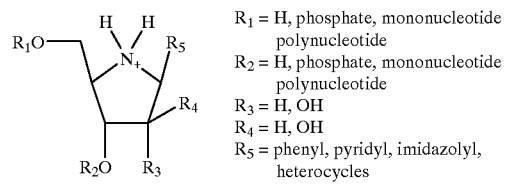

$R_1$ = H, phosphate, mononucleotide polynucleotide
$R_2$ = H, phosphate, mononucleotide polynucleotide
$R_3$ = H, OH
$R_4$ = H, OH
$R_5$ = phenyl, pyridyl, imidazolyl, heterocycles wherein R1 is hydrogen, phosphoryl, mononucleotide in phosphodiester bonding to the oxygen of R1-O, or polynucleotide in phosphodiester bonding to the oxygen of R1—O; R2 is hydrogen, phosphoryl, mononucleotide in phosphodiester bonding to the oxygen of R1—O, or polynucleotide in phosphodiester bonding to the oxygen of R1—O; R3 is hydrogen or hydroxy, R4 is hydrogen or hydroxy; and R5 is hydrogen, phenyl, pyridyl, imadazolyl, adenine, quanine, pyrimidine, or an ortho, meta or para substituted phenyl.

When R5 is a phenyl group, examples of phenyl groups include, but are not limited to, nitrophenyl, aminophenyl, fluorophenyl, chlorophenyl, bromophenyl, hydroxyphenyl, and carboxyphenyl.

Examples of the compounds of this invention are as follows:

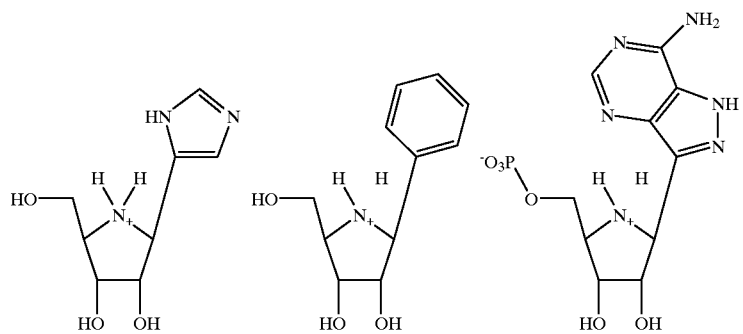

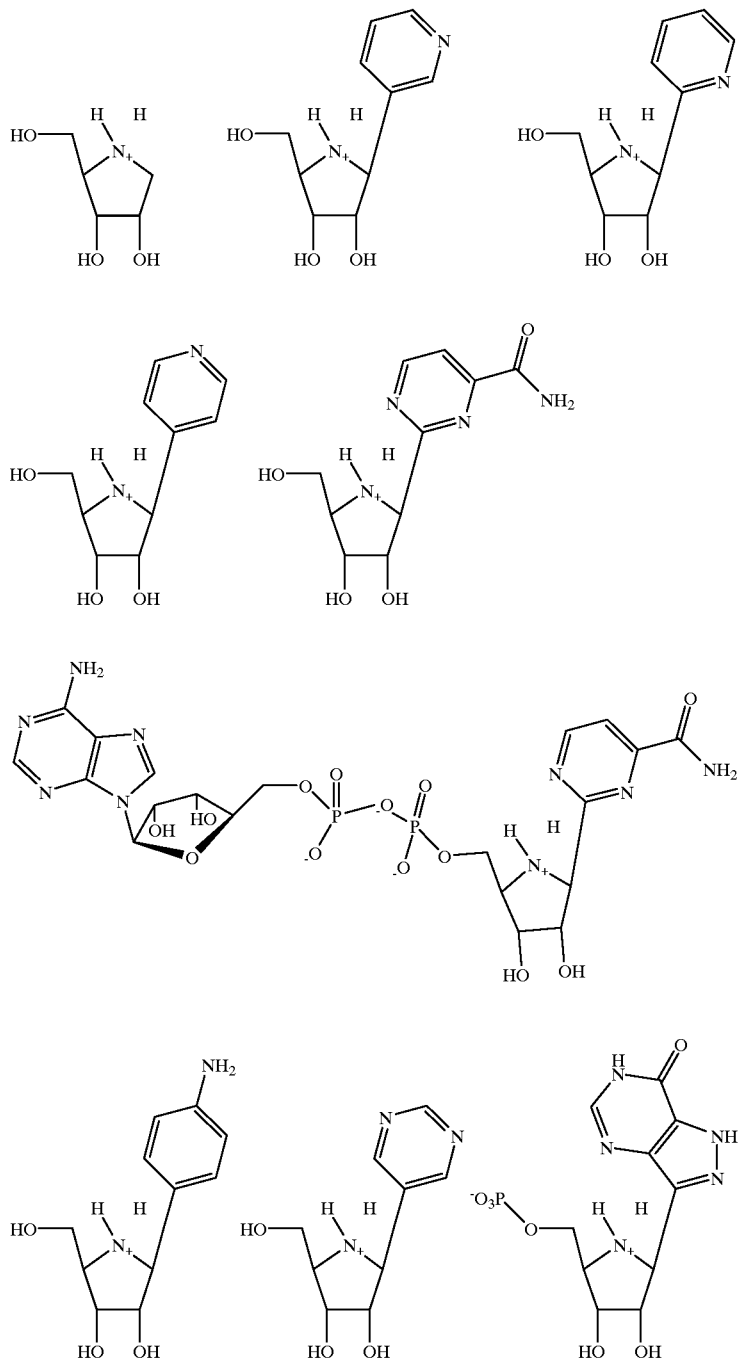

-continued

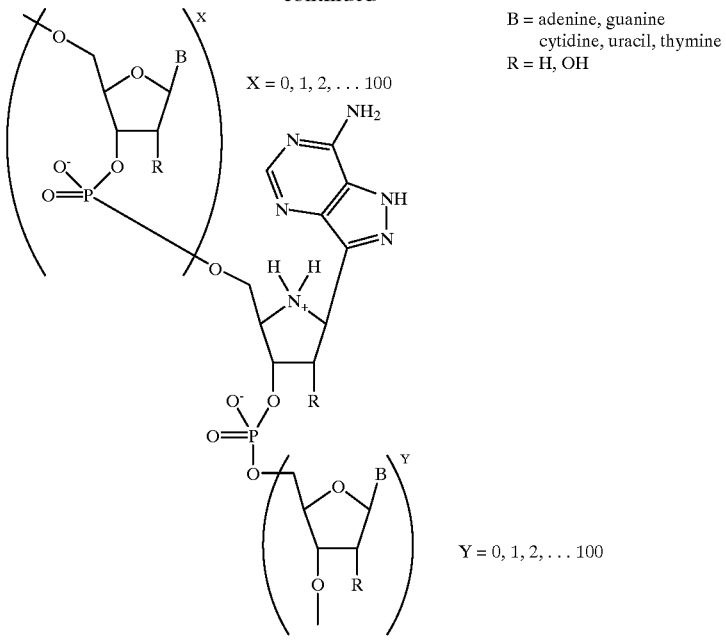

B = adenine, guanine
cytidine, uracil, thymine
R = H, OH

X = 0, 1, 2, ... 100

Y = 0, 1, 2, ... 100

The transition-state inhibitor analog compounds of this invention are effective in the treatment of infections and diseases which involve nucleoside hydrolaze and the transferase enzyme activity of parasites, including protozoa and helminth parasites, which infections and diseases include dysentary, giardiasis, vaginitis, leichmaniasis, Chagas disease, sleeping sickness, malaria, schistosomiasis, filariae disease, onchocerciosis, loiasis and infections caused by hookworm, pinworm, tapeworm and roundworm.

The bacterial toxins against which the compounds of this invention are effective include cholera toxin, dyphtheria toxin, pertussis toxin, tetanus toxin, botulinum toxin, E. coli enterotoxin Pseudomonas enterotoxin and other ADP-ribosylating toxins. In addition, the compounds of this invention are effective against plant toxins, such as ricin, as well as other toxins used in cancer chemotherapy.

The transition-state analog inhibitor compounds of this invention inhibit the activity of enzymes including nucleoside hydrolases, deoxynucleoside hydrolases, ADP-ribosyltransferases and RNA and DNA N-glycohydrolases.

The present invention provides for a method for treating a subject having parasitic infection or disease comprising administering to the subject a compound of the present invention in an amount effective to treat the infection or disease.

Non-limiting examples of parasitic infections or diseases which may be treated include those selected from the group consisting of dysentary, giardiasis, vaginitis, leichmaniasis, Chagas disease, sleeping sickness, malaria, schistosomiasis, filariae disease, onchocerciosis, loiasis and infections caused by hookworm, pinworm, tapeworm and roundworm.

Further provided by the present invention is a method for treating a disease or condition caused by a toxin in a composition comprising contacting the composition with a compound of the present invention in an amount effective to treat the disease or condition caused by the toxin.

Non-limiting examples of toxins include those selected from the group consisting of cholera toxin, diphtheria toxin, pertussis toxin, E. coli enterotoxin, Pseudomonas enterotoxin, tetanus toxin, botulinum toxin and plant toxins including ricin and other toxins used in chemotherapy.

The present invention also provides for a pharmaceutical composition comprising a compound of the present invention.

Further provided by the present invention is a method of treating a composition to inactivate a parasite or toxin present therein comprising contacting the composition with a compound of the present invention in an amount effective to inactivate the parasite or toxin. Non-limiting examples of toxins which may be inactivated by the method of the present invention include those selected from the group consisting of cholera toxin, diphtheria toxin, pertussis toxin, E. coli enterotoxin, Pseudomonas enterotoxin, tetanus toxin, botulinum toxin and plant toxins including ricin and other toxins used in chemotherapy. Non-limiting examples of diseases caused by a parasite which maybe inactivated by the method of the present invention include those selected from the group consisting of dysentary, giardiasis, vaginitis, leichmaniasis, Chagas disease, sleeping sickness, malaria, schistosomiasis, filariae disease, onchocerciosis, loiasis and infections caused by hookworm, pinworm, tapeworm and roundworm.

Examples of compositions that can be contacted with a compound of the present invention to inactivate a parasite or toxin include, but are not limited to, blood, blood derivatives, plasma, water and milk.

In order to determine the steric and bonding properties of nucleoside hydrolase enzymes so that the inhibitor compounds of this invention could be developed, colorimetric assays for nucleoside hydrolase and purine nucleoside phosphorylase catalytic activity were performed. The activity for nucleoside hydrolase was determined at 30° C. by the formation of reducing sugar from 5 mM inosine in 50 mM Hepes, pH 7.3. The assay volumes were 200–800 ml. The reaction was terminated by the addition of 100 ml of 1.0 M HCl. After the reaction was stopped, the reducing sugar was measured by the addition of 100 ml of 1.05 M NaOH, 0.3 ml of reagent containing 4% $Na_2CO_3$, 1.6% glycine, and 0.045% $CuSO_4.5 H_2O$, and 0.3 ml of 0.12% 2.9-dimethyl-1,10-phenanthroline, in a total volume of 1.6 ml. The color was developed at 95° C. for 8 minutes and the optical absorbance measured at 450 nm. Enzymatic activity was expressed as millimoles of reducing sugar formed per minute per milligram of protein. During the initial stages of purification a modified assay which removes excess protein was used. Protein solutions of 1–5 ml were added to 100 ml of the assay mixture and incubated for the desired time. The assay was terminated by the addition of 100 ml of 0.1 M $ZnSO_4$. Excess $Zn^{2+}$ was removed by the addition of 100 ml of 0.1 M NaOH. After centrifugation, 250 ml of supernatant was removed and assayed for reducing sugar. Assays for purine nucleoside phosphorylase were the same as for nucleoside hydrolase except that 10 mM sodium arsenate was added as the phosphate analogue. Arsenate readily replaces phosphate in the reaction and the product ribose 1-arsenate rapidly hydrolazes to release ribose which is detected in the reducing sugar assay.

To perform a spectrophotometric assay for nucleoside hydrolase, reaction mixtures of 1.0 ml contained inosine, 50 mM Hepes, pH 7.3, and the desired concentration of inhibitor. At other pH values, a mixed buffer system was used which contained 30 mM each of acetate. Mes, Pipes, Hepes, Bicine, and Ches were adjusted to the desired pH with HCl or NaOH. The reaction was initiated with a small volume of enzyme and the increase in absorbance recorded at 280 nm. Conversion of a 1 mM solution of inosine to products resulted in a change in absorbance of 0.92 at 280 nm and pH 7.3. The millimolar extinction coefficient varied from 0.98 to 0.58 over the pH range of 5–10. A standard curve of extinction coefficients was used to determine the rates at specific pH values, since the extinction coefficient is not a linear function of pH.

A radioactive assay for nucleoside hydrolase catalytic activity was determined by the conversion of $[8\text{-}^{14}C]$inosine to $[8\text{-}^{14}C]$hypoxanthine and ribose. Assay mixtures of 19 ml contained the desired concentration of inosine and inhibitor(s) together with approximately $3\times10^4$ cpm of radioactive inosine in 50 mM Hepes or triethanolamine buffer, pH 7.3. Reactions were initiated by the addition of 1 ml of nucleoside hydrolase in 0.5 M Hepes or triethanolamine, pH 7.3. Samples of 3 ml were removed at the appropriate intervals and spotted on polyethyleneimine cellulose thin layer plates which had been previously spotted with 4 ml of a solution containing 2.2 mM each of inosine and hypoxanthine. Control experiments in which the labelled inosine was prespotted on the thin layer plates established that application of the reaction mixture to the ion-exchange resin stopped the reaction.

HPLC and NMR assays were used to determine substrate activity substrate activity was determined in incubation mixtures containing nucleosides at 2.5–28 mM in the presence of 50 or 100 mM triethanolamine-HCl, pH 8.0, or 50 mM potassium phosphate, pH 7.5, and 16–400 mg/ml purified nucleoside hydrolase. Reaction mixtures were incubated for 5–27 hours and samples analyzed on a 7.8 mm×30 cm $C_{18}$-HPLC column eluted with 5 or 10% methanol in $H_2O$, 4 ml/minute. Samples were detected by the absorbance at 257 nm. Substrate activity with deoxyinosine was also measured at 500 MHz by NMR. The sample contained 14 mM deoxyinosine, 50 mM triethanolamine-HCl, pH 8.0, in $D_2O$. After collecting the reference proton spectrum, 290 mg/ml nucleoside hydrolase was added via a syringe fitted with an extension tube. Proton NMR spectra were collected in sets of eight scans over 15 minutes at room temperature.

Protein was routinely estimated by the dye-binding method of Bradford. Reagents were purchased from Bio-Rad and bovine serum albumin was used as the standard. The extinction coefficient and absolute concentration of enzyme was determined by quantitative analysis of samples which had been dialyzed against 1 mM potassium phosphate buffer, pH 7.3, and dried at 80° C. under reduced pressure to constant mass. Samples of enzyme and dialysate were analyzed in triplicate on a Cahn ultrabalance.

*C. fasciculata* were grown on 1.3% sucrose, 0.4% tryptone, 0.5% yeast extract, 0.1% triethanolamine, 2 mg/liter hemin, and a vitamin mixture consisting of one A to Z multivitamin-multimineral tablet (A & P Supermarkets) per 16 liters of medium. The vitamin tablets were ground, suspended in 50% ethanol, and added to the sterile medium just before innoculation. Tetracycline (20 mg/liter) and 30 mg/liter chloramphenicol were also added prior to innoculation. When sequential batches were grown, the tetracycline-chloramphenicol mixture was alternated with 50 mg/liter ampicillin and 25 mg/liter streptomycin. Cells were cultured in a 300-liter fermenter. Cell yields were approximately 5 g/liter in normal aerated cultures and increased to near 10 g/liter when the pH was maintained at 7.2 with 10 M NaOH. Cells were harvested by continuous flow centrifugation, and flushed from the centrifuge with an equal volume of 50 mM potassium phosphate, pH 7.2, containing 2 mM inosine, 0.1 mM EDTA, 0.1 mM dithiothreitol, 1 mM benzamidine, 1 mM 1,10-phenanthroline, 50 mM phenylmethylsulfonyl fluoride, 2 mg/liter leupeptin, 50 mg/liter soybean trypsin inhibitor, and 50 mg/liter aprotinin. Cells were used directly following harvest or were frozen by placing in a −70° C. freezer. Additional benzamidine (2 mM), 100 mM phenylmethylsulfonyl fluoride, 1 ml/ml pancreatic DNase, and 1 mM $MgCl_2$ were added just before cells were disrupted.

In order to perform synthesis of labeled nucleosides, $[8\text{-}^{14}C, 5'\text{-}^3H]$AMP was synthesized from $[6\text{-}^3H]$glucose and $[8\text{-}^{14}C]$adenine by the sequential actions of hexokinase, glucose-6-phosphate dehydrogenase, 6-phosphogluconate dehydrogenase, phosphoriboisomerase, 5-phosphoribosyl-1-pyrophosphate synthetase, and adenine phosphoribosyl transferase. The reaction mixture of 1 ml contained 50 mM potassium phosphate and 50 mM triethanolamine, pH 7.0, 0.5 mM glucose, 20 mCi of $[6\text{-}^3H]$glucose, 34.9 Ci/mmol, 0.5 mM ATP, 2.5 mM $MgCl_2$, 0.4 mM adenine, 16 mCi of $[8\text{-}^{14}C]$adenine, 49 mCi/mmol, 1.1 mM NADP+ and 5 mM P-enolpyruvate. The reaction was initiated by the addition of a mixture of glucose-6-phosphate dehydrogenase, 6-phosphogluconate dehydrogenase, pyruvate kinase, hexokinase, adenylate kinase, and phosphoriboisomerase. After several minutes at 37° C., 5-phosphoribosyl-1-pyrophosphate synthetase and adenine phosphoribosyl transferase were added and the progress of the reaction monitored by HPLC-$C_{18}$ mBondapak eluted with 65 mM ammonium phosphate, pH 5.0, in 10% methanol. When the conversion of adenine to ATP stopped after approximately 60 minutes, the reaction was placed in a 95 ° C. water bath for 4 minutes. After cooling, 5 mM glucose, hexokinase, and adenylate kinase were added, incubated for 1 hour at 37° C., overnight at 5° C., and placed at 95° C. for 4 minutes. The products were purified on a 1×100-cm column of G-10 Sephadex eluted with 20 mM acetic acid. Overall yield of $[8\text{-}^{14}C, 5'\text{-}^3H]$AMP was 11.1 mCi with respect to $[8\text{-}^{14}C]$ adenine (69%) and 13.3 mCi with respect to $[6\text{-}^3H]$glucose (67%). The material was lyopholized and stored at −70° C. in 50% ethanol. The product $[8\text{-}^{14}C, 5'\text{-}^3H]$AMP was converted to labeled adenosine with alkaline phosphatase. Labeled adenosine was converted to inosine with adenosine deaminase. The double-labeled nucleosides were purified by chromatography on $C_{18}$ reverse phase HPLC with 10 mM ammonium acetate, pH 5.0, in 1% methanol as the mobile phase.

To determine nucleoside uptake in *C. fasciculata* cells were grown at 30° C. in small shaken flasks using 10 ml of the medium. After reaching an absorbance of 1–2 at 600 nm, approximately 2 mCi of [8-$^{14}$C, 5'-$^{3}$H]inosine or [8-$^{14}$C, 5'-$^{3}$H]adenosine was added, as $^{14}$C. The amount of labelled inosine or adenosine added to the culture medium represented less than 0.6% of the $A_{259}$-absorbing material present in the medium from the yeast extract. Cells were grown to an absorbance of 3–4 at 600 nm in the presence of the labeled nucleosides. Cells from 4.0 ml of culture were centrifuged for 10 minutes at 4° C. and washed twice in 10 mM potassium phosphate, pH 7.4, containing 0.9% NaCl. Nucleic acids were extracted by the addition of 1 ml of 10 mM EDTA and 1 ml of 0.1 M sodium acetate, pH 5.09, in 0.5% sodium dodecyl sulfate. Buffer-equilibrated phenol (2 ml) was added followed by 2 minutes of agitation. Following centrifugation, the upper aqueous phase was transferred to a tube containing 440 ml of 1 M tris-HCl, pH 8.0, and 180 ml of 5 M NaCl. Two volumes of ice-cold ethanol were added, and the nucleic acids collected following centrifugation. The dried pellets were dissolved in 250 ml of 10 mM Tris-HCl, pH 8.0, containing 1 mM EDTA. Samples of 100 ml were counted in 10 ml of scintillation fluid. All experiments were run in triplicate, including the growth of cells, cell labeling, and analysis of labeled nucleic acids.

In order to purify nucleoside hydrolase, freshly harvested or frozen cells were satisfactory for the preparation of nucleoside hydrolase. Approximately 1.5 kg of cells were used for each enzyme preparation. The cell suspension in the buffer and protease inhibitors described above was adjusted to pH 6.9–7.2 NaOH. The cells were disrupted in a Dynomill continuous-flow bead mill at 3000 rpm, using 0.4 mm glass beads. The disruption chamber was cooled by circulating external fluid at −20° C. The disrupted cell suspension was warmed to 55–60° C. for 5–10 minutes, chilled on ice to 4° C., and centrifuged for 90 minutes at 20,000×g in the cold. Solid ammonium sulfate was added to the supernatant to give 0.35 saturation at 4° C., stirred for 30 minutes and centrifuged at 5° C. at 20,000×g for 20 minutes. The supernatant was brought to 0.57 saturation with additional ammonium sulfate and treated as above. The resulting pellet was suspended in sufficient volume to make a suspension, but less than required to completely dissolve the pellet, using 50 mM Hepes, pH 7.2, and containing 100 mM KCl, 100 mM dithiothreitol, and 100 mM EDTA. The sample was dialyzed overnight against the buffer used to suspend the fraction.

The dialyzed fraction was applied to a 5×32 cm column of DEAE-Sephadex A-50 which was equilibrated against the buffer used to suspend the ammonium sulfate pellet. The column was washed with 1 liter of the buffer and the enzyme eluted with a 4-liter linear gradient of 0.1–0.3 M KCl in the same buffer. The enzyme eluted near 0.25 M KCl. In some preparations, 2 mM inosine was added to all buffers during ion-exchange chromatography. Only small improvements in recovery were experienced in the presence of inosine. The fractions which contained nucleoside hydrolase activity were pooled and concentrated to 70 ml using an Amicon Diaflow ultrafiltration concentrator which retained proteins with M, greater than 10,000.

The concentrated sample from ion-exchange chromatography was dialyzed against buffer containing 10 mM Hepes and 10 mM Pipes, pH 6.5. The dialyzed fraction was centrifuged to remove precipitated protein and was then applied to a 3.5×6 cm column of Procion Red HE3B (MatrexT Gel Red A, Amicon) previously equilibrated with the Hepes Pipes buffer. The column was washed with 100 ml of the buffer and the protein was eluted with a 400 ml linear gradient from pH 6.5 to 8.0. The enzyme eluted near pH 7.0. The enzyme-containing fractions were concentrated to 2 ml using a collodion bag with M 25,000 retention and the pH adjusted to 6.5.

The enzyme solution was applied to a second Red A column of 1.2×17 cm which had been previously equilibrated with 10 mM Hepes and 10 mM Pipes, pH 6.5. The column was washed with 25 ml of the buffer, and the enzyme was eluted with a 200 ml linear gradient of 0–2 M KCl. The enzyme eluted near 0.7 M KCl. The fractions containing enzyme were concentrated to approximately 1 ml and dialyzed against 0.5 M Hepes, pH 7.5. Purity of the protein was estimated by electrophoresis in polyacrylamide gels containing sodium dodecyl sulfate. Enzyme of adequate purity was rapidly frozen using dry ice ethanol in small glass tubes and stored at −70° C. In cases where the enzyme was of inadequate purity following this procedure, it was subject to gel filtration on a 2.5×63 cm column of Superdex 200 in 50 mM potassium phosphate, pH 7.5, using a flow rate of 2 ml/min.

The elution position of active nucleoside hydrolase relative to proteins of known molecular weight was determined by Ultragel AcA34 gel filtration. Bovine serum albumin (M=66,000), β-amylase (M=66,000), β-amylase (M=200,000), carbonic anhydrase (M=29,000), and alcohol dehydrogenase (M=150,000) were used as protein standards. Approximately 200 ml of a 15 mg/ml solution of each protein was passed through a 2×26 cm column equilibrated with 100 mM triethanolamine, pH 7.5, containing 50 mM KCl and 0.02% sodium azide. The columns were run at room temperature. The protein peaks were monitored at 280 nm, and the elution volume was determined from the position of the protein peak. The void volume of the column was determined in a separate experiment using blue dextran. The ratio of elution position of the proteins relative to that of the void volume was determined graphically, and the molecular weight for nucleoside hydrolase was estimated relative to the molecular weight standards.

Reaction mixtures contained 50 mM Hepes, pH 7.5, 10 mM hypoxanthine, 1–3 M ribose, and 27 mg/ml nucleoside hydrolase at 37° C. Samples of 25 ml were acidified with 25 ml of 1 M HCl at the desired times and neutralized with 25 ml of 1.05 M NaOH. Samples were analyzed in triplicate by reverse-phase chromatography on an Altex ODS analytical HPLC column eluted with 90 mM ammonium phosphate, pH 5.0, in 1% methanol. Areas under the hypoxanthine and inosine peaks were integrated to quantitate the distribution at equilibrium.

To determine the methanolysis reaction, to a solution of 1 g of recrystallized inosine in 125 ml of 8 mM potassium phosphate, pH 8.2, in 20% methanol was added 0.5 mg of nucleoside hydrolase. Hydrolysis of inosine at 30° C. was monitored by HPLC. When the reaction was 30% complete, the sample was heated to 100° C., concentrated, and cooled on ice. Hypoxanthine and unreacted inosine were removed by filtration. The filtrate was concentrated to a colorless syrup, dissolved in $D_2O$ and exchanged into $D_2O$ by two additional exchanges of 3 ml each. Analysis of the product was by $^1H$ NMR at 500 MHz. Only ribose and inosine resonances were observed. This shows that hypoxanthine was efficiently removed.

Next, enzymatically synthesized [8-$^{14}$C, 1'-$^{3}$H]AMP was prepared with a $^{14}$C/$^{3}$H ratio of 2.46±0.02 and converted enzymatically to labeled adenosine and inosine with the same specific radioactivity. Cultured *C. fasciculata* readily incorporated labeled inosine and adenosine from the medium. Approximately 5% of the total added label was incorporated in 1–2 cell doublings at cell densities above 1.0 absorbance unit at 600 nm. Isolated nucleic acids demonstrated an increase in the $^{14}C/^{3}H$ ratio to 5.2±0.9 with [8–$^{14}C$, 5'-$^{3}H$]inosine and to 5.2±0.3 with [8-$^{14}C$, 5'-$^{3}H$] adenosine. Salvage of these nucleosides indicated greater than 2-fold enrichment of base relative to ribose in the nucleic acids. The results of nucleoside uptake experiments are summarized in Table I below.

TABLE I

Incorporation of labeled inosine and adenosine into nucleic acids of C. fasciculata

| Labeled substrate | $^{14}C/^{3}H$ ratio nucleosides[A] | $^{14}C/^{3}H$ ratio RNA and DNA |
|---|---|---|
| [8-$^{14}C$,5'-$^{3}H$]Inosine | 2.46 ± 0.02 | 5.2 ± 0.9 |
| [8-$^{14}C$,5'-$^{3}H$]Adenosine | 2.46 ± 0.02 | 5.2 ± 0.3 |

[A]The ratios of $^{14}C/^{3}H$ in the nucleosides are identical since labeled inosine and adenosine were synthesized from the same preparation of [8-$^{14}C$,5'-$^{3}H$]AMP To determine purine nucleoside phosphorylase activity, cell extract from C. fasciculata was dialyzed against phosphate-free buffer and assayed for the presence of purine nucleoside phosphorylase by measuring the rate of formation or ribose from 5 mM inosine in assay mixtures with and without inorganic arsenate. In the absence of arsenate, the specific activity of inosine hydrolase activity was 87±4 nmol/min/mg protein. In the presence of inorganic arsenate, the total activity for glycoside bond hydrolysis was 98±12 nmol/min/mg protein. Thus, the activity of purine nucleoside phosphorylase was not significant compared with the nucleoside hydrolase activity in dialyzed cell extracts of C. fasciculata.

For the purification of nucleoside hydrolase, which is resistant to heat denaturation at 55–60° C., heat treatment was performed, which provided a convenient first step and gave 7-fold purification. Although ammonium sulfate fractionation provided only 2-fold purification, it was useful to concentrate the enzyme to a reasonable volume for subsequent dialysis. The major purification resulted from ion-exchange and dye-column chromatography. Purifications of 9- and 6-fold, respectively, were obtained on DEAE ion-exchange chromatography and the first Red A column. The remaining impurity was removed by elution from a second column of Red A gel and, when necessary, by gel-exclusion chromatography. The enzyme exhibits pH dependence of elution on Red A gel. This step was unusually effective for nucleoside hydrolase and often provided enzyme which was nearly pure. The purification following the Red A columns resulted in enzyme which was typically >95% homogeneous as determined by gel electrophoresis on denaturing polyacrylamide. See FIG. 1. Following gel exclusion chromatography, the majority of the fractions were >99% homogeneous. The enzyme was typically purified 1000-fold from cell extracts in 13% yield as summarized in Table II below. The extinction coefficient for purified enzyme was 0.569 at 280 nm for a 0.1% solution in 1 mM potassium phosphate, pH 7.3. The ultraviolet absorbance spectrum exhibited a maximum at 278 nm and was characteristic of a protein with a low molefraction of tryptophan.

TABLE II

Purification of nucleoside hydrolase from Crithidia fasciculata

| Purification | Volume ml | Protein mg | Units mmol/min | Specific activity mmol/min/mg |
|---|---|---|---|---|
| Initial extract[A] | 3300 | | | 0.05 |
| Heat treatment | 1960 | 9800 | 3600 | 0.37 |
| (NH$_4$)$_2$SO$_4$ | 310 | 4000 | 2900 | 0.72 |
| DEAE-A-50 | 190 | 147 | 927 | 6.3 |
| Red A. pH elution[A] | 2 | 13 | 468 | 36 |
| Red A. KCl elution[B] | 1 | 10 | 470 | 47 |

[A]A sample of the initial extract was centrifuged and assayed to determine the specific activity. The remainder was used directly for the next step. Starting material was 1.2 kg of frozen C. fasciculata.
[B]The fractions were concentrated to give these volumes. The purified enzyme is >97% homogeneous by sodium dodecyl sulfate-polyacrylamide gel electrophoresis at specific activity 47.

Figure 2:
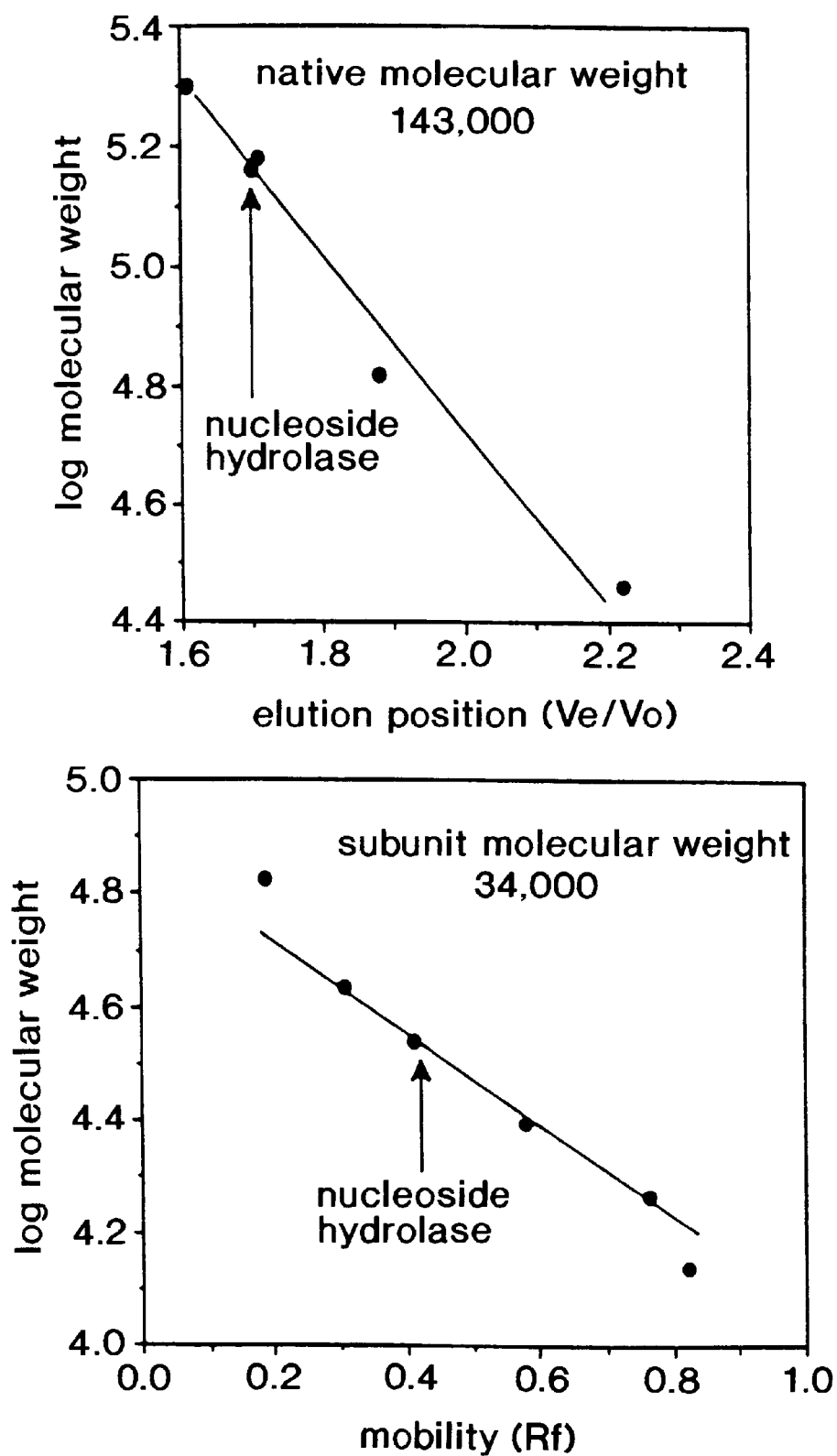
FIG. 2 represents the molecular weight estimation for nucleoside hydrolase. The upper panel shows the elution position of native nucleoside hydrolase relative to proteins of known molecular weight. The elution position of nucleoside hydrolase was determined by catalytic activity. The lower panel shows the relative mobility of nucleoside hydrolase relative to proteins of known molecular weight on polyacrylamide gel electrophoresis containing sodium dodecyl sulfate.

The molecular weight of active enzyme was estimated by gel-exclusion chromatography and by denaturing gel electrophoresis using proteins of known masses as standards. Nucleoside hydrolase eluted at an apparent molecular weight of 143,000 on gel exclusion chromatography. See FIG. 2. Gel electrophoresis on denaturing polyacrylamide gave a single molecular weight species with an apparent subunit molecular weight of 34,000. These values are consistent with the active enzyme being composed of four subunits with identical or highly similar molecular weight.

Substrate specificity of nucleoside hydrolase was determined. The commonly occurring purine and pyrimidine ribonucleosides are substrates with $V_{max}/K_m$ values which range from $3.4 \times 10^3$ to $1.7 \times 10^5$ $M^{-1}S^{-1}$. The $V_{max}$ values are greatest for the pyrimidine nucleosides, while the purine nucleosides have the lower $K_m$ values. No cooperativity was observed in the substrate saturation curves. Normal initial rate curves were obtained with no lags or hysterisis. The turnover numbers for naturally occurring nucleosides varied from 2 $s^{-1}$ for guanosine to 243 $s^{-1}$ for 5-methyluridine. Purine riboside was a poor substrate with a $V_{max}/K_m$ of $1.5 \times 10^2$ $M^{-1}$ $S^{-1}$ a $K_m$ of 145 mM, and a turnover number of 0.023 $S^{-1}$. Deoxynucleosides at the 2'-, 3'- or 5'-positions were poor substrates, or lacked substrate activity. In several cases the deoxynucleosides are inert at $<10^{-4}$ the rates for hydrolysis of inosine. An example of the effect of the 2'-hydroxyl is the comparative reactivity of 5-methyluridine and thymidine, where the apparent $V_{max}$ difference was $>10^5$, with no activity being detected for thymidine. Substitution of the 5'-hydroxyl with phosphate or replacement with the thiomethyl group also decreased or eliminated substrate activity. Although the specificity for the aglycone was low for the substrate nucleosides, certain features of the aglycone were crucial, since tubercidin (7-deazaadenosine) was not a substrate at a detection level of $3 \times 10^{-4}$ the rate with inosine.

Product inhibition with both ribose and hypoxanthine resulted in slope-linear, competitive patterns. The K, slope values were 0.70±0.10 and 6.2±0.9 mM, respectively, for ribose and hypoxanthine. When both ribose and hypoxanthine were added in combination and the initial rates estimated using radioactive inosine as substrate, the slope increased less than expected for the combination of both inhibitors. These results indicated that the products combined in an antagonistic manner, with the combination of one decreasing the affinity for the second. The dissociation constant for interaction by hypoxanthine with the enzyme-ribose complex for interaction of hypoxanthine with the enzyme-ribose complex could not be measured accurately because of the limited solubility of hypoxanthine.

Tubercidin (7-deazadenosine) was a competitive inhibitor of nucleoside hydrolase with a $K_{is}$ of 2,300 mM. Apparent inhibition constants ($K_{i(app)}$) were determined from the relationship shown in the following equation:

$$V_o/V_i + (\text{inosine} \pm K_m(1+I/K_{i(app)})/(\text{inosine}+K_m)$$

where $V_o$ and $V_i$ are the initial reaction rates without and with inhibitor, respectively. $K_m$ is the Michaelis constant for inosine, I is inhibitor concentration and $K_{i(app)}$ is the apparent dissociation constant for inhibitor. In cases where the inhibitor is competitive with respect to substrate, $K_{i(app)}$ is the dissociation constant for the enzyme-inhibitor complex. Inhibition constants obtained by this method are summarized in Table III below. Nucleosides and nucleoside analogues which are not substrates are poor inhibitors of nucleoside hydrolase compared with the substrates, with most nucleosides having inhibition constants in the millimolar range.

TABLE III

Kinetic constants for substrates and inhibitors of nucleoside hydrolase

| Substrate or inhibtor | $V_{max}$ $\mu$mol min$^{-1}$ mg$^{-1}$ | $K_m$ uM | $V_{max}/K_m$ M$^{-1}$ S$^{-1}$ | $K_{is}$ or $K_{i(app)}$ uM |
|---|---|---|---|---|
| Inosine | 50 ± 2 | 380 ± 30 | 7.6 × 10$^4$ | |
| Adenosine | 7.6 ± 0.2 | 480 ± 30 | 9.8 × 10$^3$ | |
| Guanosine | 70 ± 0.04 | 420 ± 10 | 3.4 × 10$^3$ | |
| Purine riboside | 0.04 ± 0.01 | 145 ± 23 | 1.5 × 10$^2$ | |
| 5-Methyluridine | 380 ± 5 | 1,300 ± 40 | 1.7 × 10$^5$ | |
| Uridine | 255 ± 3 | 1,220 ± 40 | 1.2 × 10$^6$ | |
| Cytosine | 36 ± 3 | 4,700 ± 500 | 4.5 × 10$^3$ | |
| Ribose[a] | | | | 700 ± 40 |
| Hypoxanthine[a] | | | | 6,200 ± 900 |

| Substrate or inhibitor | Substrate or inhibitor concentration[b] | $K_{is}$ or $K_{i(app)}$ $\mu$M |
|---|---|---|
| 7-Deazaadenosine[a] | <0.0008 (3) | 2,300 ± 400 |
| d-Adenosine | <0.0006 (17) | 3,200 ± 800 |
| 3'-d-Adenosine | <0.16 (7.5) | 7,290 ± 1,100 |
| d-Inosine | <0.0003 (21) | 2,300 ± 280 |
| Thymidine | <0.0008 (14) | 7,800 ± 2,200 |
| 5'-Deoxyadenosine[c] | | |
| 5'-Methylthioadenosine[c] | <0.0003 (5) | 5,700 ± 1,500 |
| Formycin B[d] | <0.02 (2.5) | 1,960 ± 410 |
| AMP | <0.01 (20) | 44,000 ± 6,000 |

[a]The inhibition constant is $K_{is}$ obtained from experiments using at least four inosine concentration at each of three inhibitor concentration. The inhibition constant was obtained to the best fit of the data to the equation for competitive inhibition.
[b]The concentration of the nucleoside used in the activity/inhibition determination. The inhibition constant $K_{i(app)}$ is an apparent constant determined at a single inosine concentration near the $K_m$ for inosine and three inhibitor concentration. The value was calculated from the ratio of −inhibitor/+inhibitor initial rates as described under "Results."
[c]Low rates of product formation were observed for both 5'-d-adenosine and 5'-d-inosine. The $K_{i(app)}$ values were measured with inosine as substrate under conditions where no product would be formed from the 5'-deoxynucleosides.
[d]Formycin B is not expected to expected to be a substrate since the compound is a C-glycoside. The N-9 and C-8 atoms of inosine are reversed to give formycin B.

Figure 3:
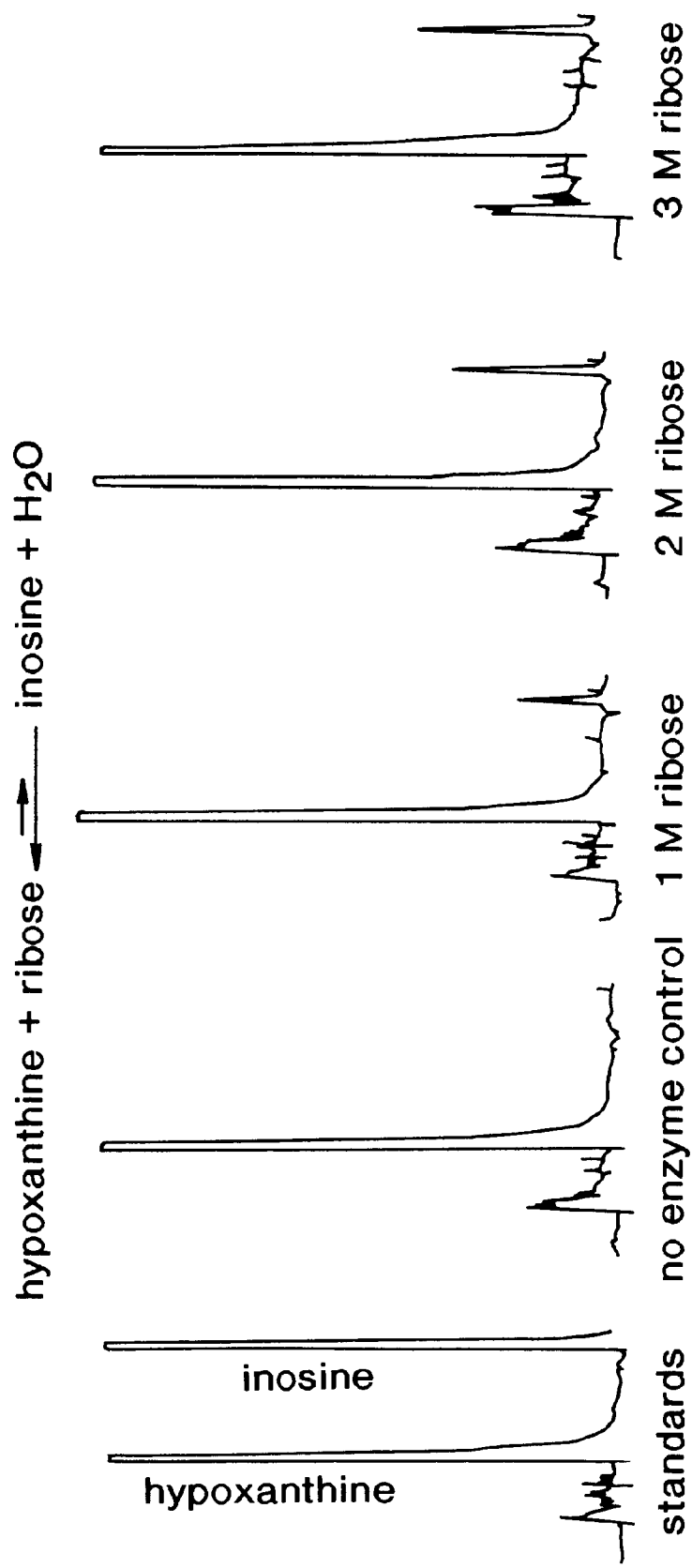
FIG. 3 represents the determination of the equilibrium constant for nucleoside hydrolase. The elution profile labeled "standards" contained a reaction mixture to which inosine was added. The elution profile labeled "no enzyme control" contained 2 M ribose in the same reaction mixture labeled "2 M ribose" and was incubated for 18 hours at 37° C. without enzymes. The elution profile labeled "1 M ribose", "2 M ribose" and "3 M ribose" demonstrate the dependence of inosine formation on the concentration of ribose. Hypoxanthine was fixed at 10 mM in all incubations.

The equilibrium constant for nucleoside hydrolase was established by the equilibrium formation of inosine from relatively high concentrations of ribose and hypoxanthine. The temperature was maintained at 37° C. to increase the solubility of hypoxanthine. At 10 mM hypoxanthine and with ribose concentration varying from 1 to 3 M, inosine was readily detected and quantitated by HPLC. The dissociation constant of 106±16 M was obtained from three experiments typified by the results of one experiment shown in FIG. 3.

Solvent reactivity was then determined. The ability of methanol to serve as a solvent nucleophile in the nucleoside hydrolase reaction was tested with inosine as the substrate and 20% methanol in water as the solvent. The limit of detection for the product of the methanolysis reaction, 1-methyl ribose, was estimated to be 5% of the total ribose product by NMR. There was no detectable resonance at the positions of authentic 1-methyl ribose. Separate experiments established the stability of inosine hydrolase under the reaction conditions.

Figure 4:
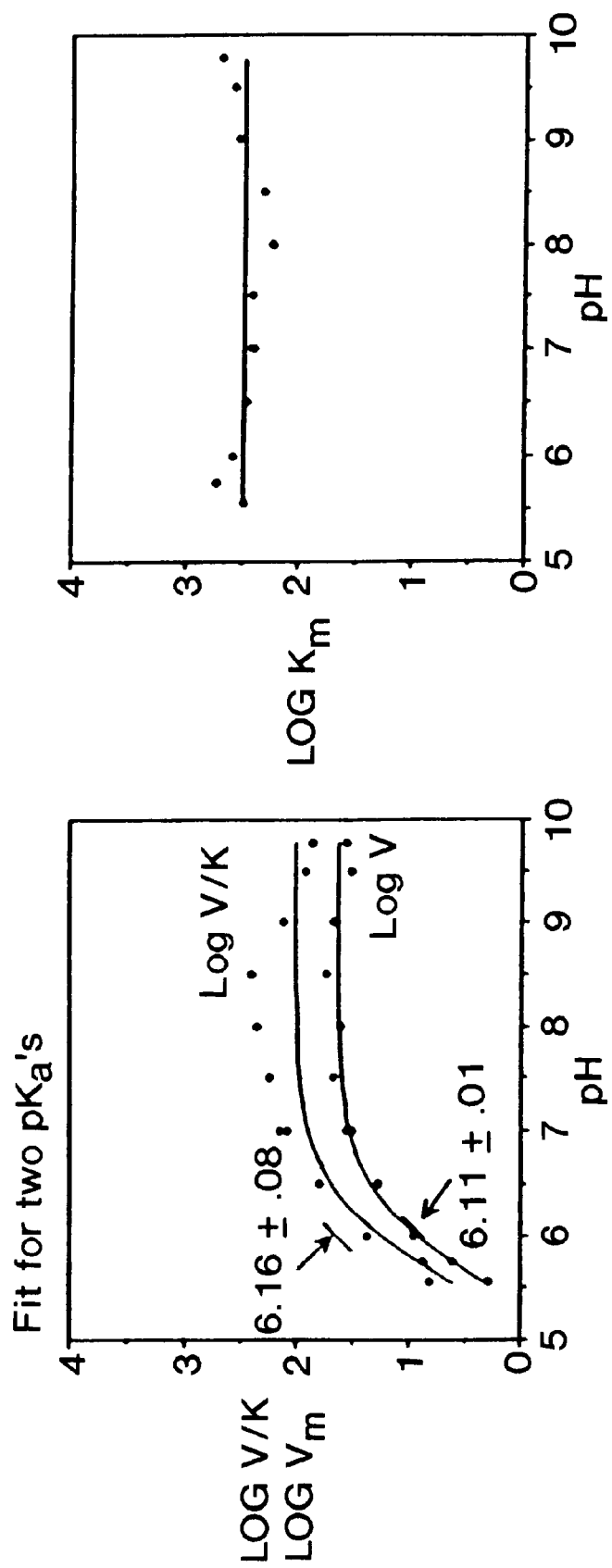
FIG. 4 represents the effect of pH on the kinetic constants for a nucleoside hydrolase. The right panel demonstrates the independence of $K_m$ value on solution pH. The data points are the best fit of the kinetic data to the Michaelis-Menten equation using the programs of Cleland. The left panel demonstrates the decrease in $V_{max}$ and $V_{max}/K_m$ at low pH values. The experimental points were taken from the best fit of the data to the Michaelis-Menten equation. The experimental lines are the best fit to the equation for two essential ionizable groups with the identical $pK_a$ values.
Figure 5:
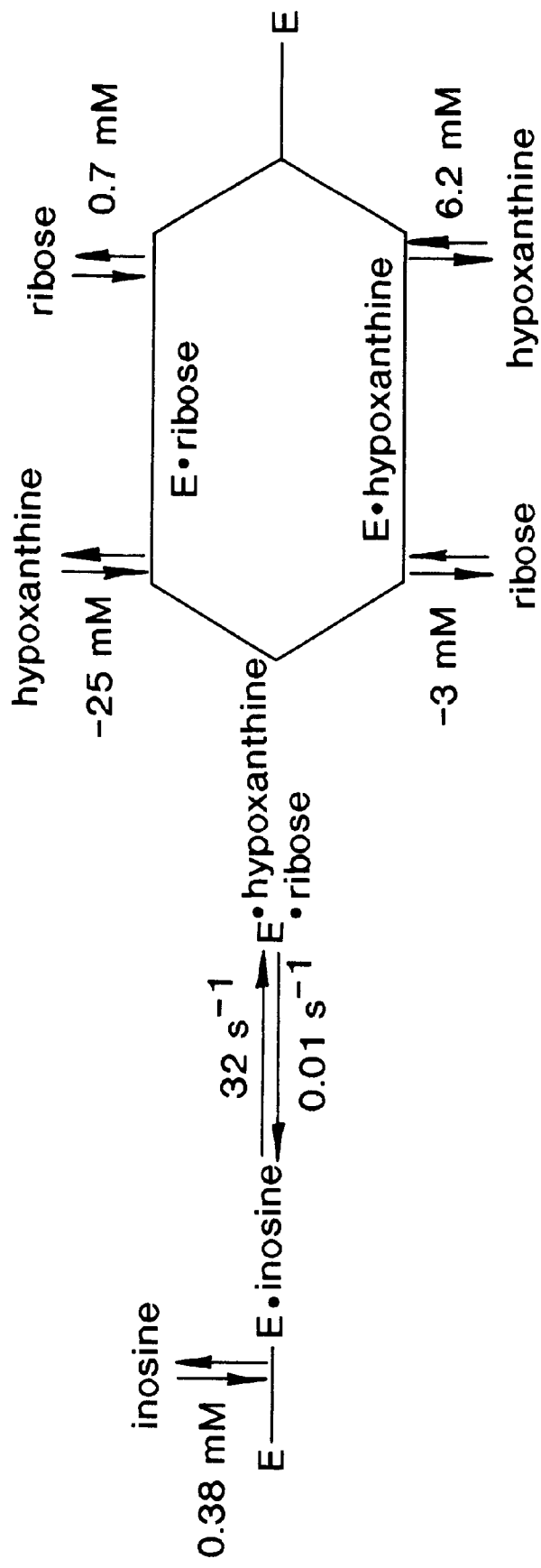
FIG. 5 represents the kinetic mechanism for nucleoside hydrolase. The concentrations shown near the arrows for binding and release of substrate and products are the dissociation constants for each complex. The rate for the interconversion of the enzyme-inosine and enzyme-hypoxanthineribose complexes are from $V_{max}$ in the forward direction and calculated from $k^{eq}$ and the Haldane equation in the reverse direction. Free nucleoside hydrolase is abbreviated as "E". The dissociation constant for ribose interacting with the "E." hypoxanthine complex is estimated from the the 3 experimentally determined dissociation constant and the expression for the thermodynamic box of product release.

The effect of pH on the kinetic constants of nucleoside hydrolase was determined. The activity of nucleoside hydrolase was stable over a wide range of pH values, permitting initial rate studies from pH 5.5 to 9.7. See FIG. 4. The observed $K_m$ for inosine was independent of pH over the entire range. The V, value was independent of pH at values above 7, but decreased rapidly at pH values below 7. The data could not be fit to a single $pK_a$ but was fit well by the equation describing two essential groups with $pK_a$ values of 6.11±0.01. Both groups must be in the unprotonated form for catalytic activity, but neither influences substrate binding. Response of $V_{max}/K_m$ to pH was parallel to that for $V_{max}$ to give two groups with $pK_a$ values of 6.16±0.08.

In order to determine the transition-state of nucleoside hydrolase, nucleoside hydrolase was purified from *C. fasciculata* as described above. All enzyme used was >95% homogeneous by denaturing gel electrophoresis.

Isotopically labeled AMP's were prepared enzymatically from appropriately labeled glucose, ribose, and adenine. Radiolabeled inosine and adenosine were prepared enzymatically from the corresponding AMP. Labeled adenosine nucleosides were prepared by treatment of the corresponding AMP with 1–2 units of calf intestine alkaline phosphatase (P-L Biochemicals) in 100 mM triethanolamine, pH 8.0 at 37° C., in the presence of 12 nM (R)-deoxycoformycin to inhibit adenosine deaminase activity. Labeled inosines were prepared by treatment of the corresponding adenosines with 3 units of adenosine deaminase (Sigma) in 100 nM triethanolamine, pH 8.0/1.5 mM MgCl$_2$, 37° C. The reactions were monitored by reverse-phase HPLC and quenched when complete by heating at 100° C. for 4 minutes. The nucleosides were purified by reverse-phase HPLC on a Waters Bondapack C$_{18}$ column at 2.0 mL/min flow rate with detection at 257 nm. Adenosine was eluted with 9.9 mM ammonium acetate, pH 5, in 1% MeOH. Inosine was purified in 9.5 mM ammonium acetate, pH 5, in 5% MeOH. Fractions containing the desired nucleoside were pooled, concentrated, and diluted to approximately 3 mCi/mL in 50% aqueous ethanol and stored at −70° C. The isotopically labeled compounds prepared for this study are listed in Table IV.

TABLE IV

Kinetic Isotope Effects for Nucleoside Hydrolase

| Substrates | isotope and type of effect[a] | exptl kinetic isotope effect[b] |
|---|---|---|
| [1'-$^3$H]inosine + [5'-$^{14}$C]inosine | 1'-$^3$H, α-secondary | 1.150 ± 0.006 (3) |
| [2'-$^3$H]inosine + [5'-$^{14}$C]inosine | 2'-$^3$H, β-secondary | 1.161 ± 0.003 (4) |
| [1'-$^{14}$C]inosine + [5'-$^3$H]inosine | 1'-$^{14}$C, primary | 1.044 ± 0.004[c] (3) |

TABLE IV-continued

Kinetic Isotope Effects for Nucleoside Hydrolase

| Substrates | isotope and type of effect[a] | exptl kinetic isotope effect[b] |
|---|---|---|
| [9,5'-$^{15}$N, $^{14}$C]inosine + [5'-$^3$H]inosine | 9-$^{15}$N, primary | 1.026 ± 0.004[c] (4) |
| [5'-$^3$H]inosine + [5'-$^{14}$C]inosine | 5'-$^3$H, δ-secondary | 1.051 ± 0.003 (4) |
| [4'-$^3$H]inosine + [5'-$^{14}$C]inosine | 4'-$^3$H, γ-secondary | 0.992 ± 0.003 (4) |
| [1'-$^3$H]adenosine + [5'-$^{14}$C]adenosine | 1'-$^3$H, α-secondary | 1.157 ± 0.003 (3) |

[a]A primary isotope effect indicates that the isotope is a bonding atom in the breaking bond. Secondary isotope effects indicate that the isotope is one (α), two (β), three (γ), of four (δ) bonds distant from the breaking bond.
[b]The number in parentheses is the number of experimental kinetic isotope effect measurements made for a kinetic isotope effect experiment.
[c]The kinetic isotope effects obtained with [5'-$^3$H]inosine as the reporter for the normal isotopic reaction rate were corrected for the 1.051 ± 0.003 isotope effect of the 5'-$^3$H. In cases where [5'-$^3$H]inosine was used as the remote label, the experimental isotope effect was corrected by the expression (observed isotope effect × 5'-$^3$H isotope effect).

Kinetic isotope effects were determined by measurement of the relative rates of hydrolysis of nucleoside containing a heavy or light (natural abundance) isotope in a given position. The substrate contained an isotopic mixture of both $^3$H and $^{14}$C species in the ribosyl residue. One radiolabel was located in the isotopically sensitive position (the heavy substitution) while the light substitution was marked by incorporation of the other radiolabel in the 5'-position of the ribosyl residue, remote from the reaction center. The [1'-$^{14}$C]- and [9-$^{15}$N]inosine kinetic isotope effects relied on [5'-$^3$H]inosine to report on the light isotope. However, a significant kinetic isotope effect was determined for [5'-$^3$H] inosine, so it was necessary to correct the [1'-$^{14}$C] and [9-$^{15}$N] kinetic isotope effects by the value of the [5'-$^3$H] kinetic isotope effect. For each kinetic isotope effect experiment, two reactions were run, one to 20–30% completion and the other to 100% completion. The 100% reaction provides the control ration of $^3$H/$^{14}$C and the 20–30% reaction provides the $^3$H/$^{14}$C ratio changed by the presence of a kinetic isotope effect. The $^3$H/$^{14}$C ratio in the product ribose was measured in order to calculate the kinetic isotope effect. As this is a trace-label technique, the information obtained from these experiments is V$_{max}$/K$_m$ kinetic isotope effects.

Kinetic isotope effects were measured by analyzing multiple samples removed from an isotope-effect reaction mixture containing $^{14}$C and $^3$H-labeled substrates. Samples were analyzed in triplicate or quadruplicate as indicated in Table IV. The $^3$H/$^{14}$C ratio was measured by scintillation counting of the product ribose following fractionation or ribose on a charcoal/cellulose column. Each cycle of the scintillation counter allowed calculation of $^3$H/$^{14}$C ratios for each sample. The average $^3$H/$^{14}$C ratios for partial and complete conversion to products were calculated and then expressed as the ratio to provide the observed kinetic isotope effect for one cycle. At least six cycles of scintillation counter analysis were used to calculate the average kinetic isotope effect for all cycles. The standard deviation of the average was calculated from the results of all cycles, from all samples.

Triethanolamine buffers, 50 mM, pH/pD 7.5 in H$_2$O/D$_2$O (99.9% D, Aldrich, were used to determine the solvent deuterium isotope effect. Inosine was employed as substrate. Initial velocity measurements were made at 30° C. measured spectrophotometrically at 280 nm, on the basis of the differential absorption of inosine and the product hypoxanthine. Differential extinction coefficients for hypoxanthine/inosine in the H$_2$O and D$_2$O solutions were determined and found to be equal, with a decrease of 0.94 OD/mmol of hypoxanthine formed. The data were fitted to the equation $$v = VA/(K(1+IVK_1) + A(1+IV_1))$$

where v=initial reaction rate, V=Vmax, A=inosine concentration, K=K$_m$, I=fractional substitution with D$_2$O, V=V isotope effect-I and VK$_1$=V$_{max}$/K$_m$ isotope effect −1 using the routines of Cleland (1977).

The BEBOVIB-IV program (Quantum Chemistry Program Exchange, No. 337, Sims et al., 1977), was used to model transition-state geometries which would provide kinetic isotope effects to match the experimentally determined values. Acceptable transition states were chemically reasonable structures which produced calculated isotope effects which simultaneously satisfied all of the experimentally determined isotope effects at positions C1', H1', H2', H4', H5', and N9. The atoms of reactant-state inosine are given in FIG. 6, together with bond lengths and geometry.

Bond lengths and angles for the reactant inosine were taken from the crystal structure. Bond lengths for C—H bonds were obtained by AMPAC calculations. Force constants for the various vibrational modes were derived from reported values (Sims & Lewis, 1984; Sims & Fry, 1974; Wilson et a., 1955). Due to limitations on the maximum number of atoms employed in a BEBOVIB model, only the relevant atoms for the transition-state structure were used. The reactant-state structure for the truncated inosine included ribosyl and imidazole ring moieties but omitted the 3'-hydroxyl group and the other hydroxylic hydrogen atoms.

The starting structure for the transition state of the ribose ring portion of inosine was derived from the X-ray crystal structure coordinates for ribonolactone. The starting C-H bond lengths were set equal to the values used for the ribose portion of inosine. The incoming oxygen nucleophile (O' in FIG. 6) was modeled as an O atom, placed 180° with respect to the breaking C1-N9 glycosidic bond. Both the forming and breaking bonds were placed orthogonal to the plane defined by the atoms attached to C1'. The calculations are insensitive to whether O or H$_2$O is used as the attacking nucleophile. AMPAC calculations were employed to estimate the bond order changes that occur in the hypoxanthine residue of inosine in proceeding to the N7-H tautomer of hypoxanthine at the transition state. The calculations were performed on 9-methylhypoxanthine and N7-H hypoxanthine. Significant changes in bond order were predicted between the bonds N9-C8-N7, while insignificant changes were observed elsewhere in the hypoxanthine ring. The sum of the bond order in the N9-C8-N7 bonds was conserved in both structures. The bond order ratio, defined as N7-C8$_{BO}$/C8-N9BO varied from 1.246 to 0.873 for the reactant and product states, respectively. This information was used to relate glycosidic C1'-N9 bond order to the bond order in the N9-C8 and C8-N7 bonds. For the reactant-state structure or inosine, where x=C$^8$-N9$_{BO}$ and 1.246x=N7-C8$_{BO}$, the sum of the bonds equals 1.246x+x=3.34, so x=3.34/2.246. Likewise, for the product structure of hypoxanthine, where x=C8-N9$_{BO}$ and 0.873x=N7-C8$_{BO}$, the sum of the bonds equals 0.873x +x=3.34, so x=3.34/1.873. In going from reactant to product, the denominator decreases by 0.373, and this amount is adjusted by the fraction of glycosidic bond cleavage=(1.051−(C1'-N$^9_{BO-TS}$))/1.051, where 1.051=C1'-N9$_{BO}$ for the reactant inosine, taken from the crystal structure, and C1'-N$^9_{BO-TS}$ is the bond order in the transition state. The bond order in the C8-N7 bond will always equal $3.34-(\text{C8-N9}_{BO})$, thus the following equations will predict the redistribution of bonds:

$$\text{C8-N9}_{BO}=3.34/(2.246-(((1.051-(\text{C1'-N9}_{BO}))/1.051)0.373))N7-\text{C8}_{BO}=3.34-(\text{C8-N}^9_{BO})$$

N7-C8-N9 of the departing hypoxanthine as the N-glycosidic bond is broken. Thus, the N7-C8 and C8-N9 bonds were varied between limiting values as a function of the fraction of cleavage of the glycosidic linkage.

The reaction coordinate was generated by coupling the stretching motion of the breaking C1'-N9 bond with the forming C1'-O' bond from the attacking oxygen. Walden inversion was incorporated into the model by introducing a weak interaction force constant of ±0.05 between the stretching modes O'-C1' and C1'-N9 with the angle bending modes defined by O'-C1'-HB1', O'-C1'-C2', O'-C1'-O4', N9-C1'-H1', N9-C1'-C2', and N9-C1'-O4'. Reaction coordinates that were generated by simple translational separation by hypoxanthine from ribose ($S_N1$-like) produced to transition states compatible with the experimental data. Transition-state space was searched by varying bond orders to atoms for which isotope effects were measured. Families of structures were obtained which were consistent with the observed kinetic isotope effects.

The kinetic isotope effects obtained with nucleoside hydrolase are summarized in Table IV. The large values observed for the secondary 1'-$^3$H and 2'-$^3$H kinetic isotope effects are indicative of a transition-state having substantial oxocarbonium ion character with sp$^2$-like hybridization at C1' and expanded bonding between N9, C1', and O'. Strong hyperconjugative interaction of H2' with C1' is necessary for the isotope effect observed with 2'-$^3$H. The maximum 1'-$^3$H kinetic isotope effect calculated for an $S_N1$ ion state with bond order approaching zero to the leaving group is approximately 1.5. The acid-catalyzed hydrolysis of inosine gives a 1'-$^3$H kinetic isotope effect of 1.20, a value which is likely to be the practical upper limit for the isotope effect at that position. Pure carbocations are unstable reactive intermediates and should closely resemble their transition states according to the Hammond postulate. However, the participation of solvent and/or active residues in the enzyme-stabilized transition state prevents formation of a fully developed carbocation. The intermediate values for the 1'-$^{14}$C and 9-$^{15}$N kinetic isotope effects indicate that the bond between C1' and N9 is not completely cleaved in the transition state.

The remote kinetic isotope effect of 1.05 from the 5'-$^3$H was much larger than previously observed for AMP nucleosidase, for a mutant form of the enzyme, or for acid-catalyzed solvolysis, all of which had values near unity. The size of this isotope effect indicates a major change in the environment of the 5' hydrogen at the transition state. An isotope effect for the 4' hydrogen of the ribosyl portion has not been previously reported for enzymatic or chemical hydrolysis of a nucleoside. The inverse nature of 0.992 for this kinetic isotope effect rules out any interaction which weakens the C4'-H4' bond or which provides addition vibrational freedom for the 4' hydrogen. Significant remote isotope effects at the 4'- and 5'-positions of inosine indicate that the enzyme-stabilized transition state contains distortions of the entire ribose ring beyond those which occur during acid-catalyzed solvolysis.

The solvent deuterium isotope effect on $V_{max}$ was found to be 1.30±0.07, and for $V_{max}/K_m$, 0.99±0.07. The observation of a solvent kinetic isotope effect indicates a small contribution from proton transfer in the step(s) which occur following binding of the substrate. The value of unity for the $V_{max}/K_m$ isotope effect indicates that the proton transfer step(s) provide no observable isotope effect between free enzyme and substrate and the first irreversible step in the reaction sequence. For nucleoside hydrolase reacting under initial rate conditions, cleavage of the glycosidic bond must be considered the first irreversible step. Proton transfer is thus not a major part of the transition state, with the proton transfer having been completed prior to transition-state formation.

Figure 7:
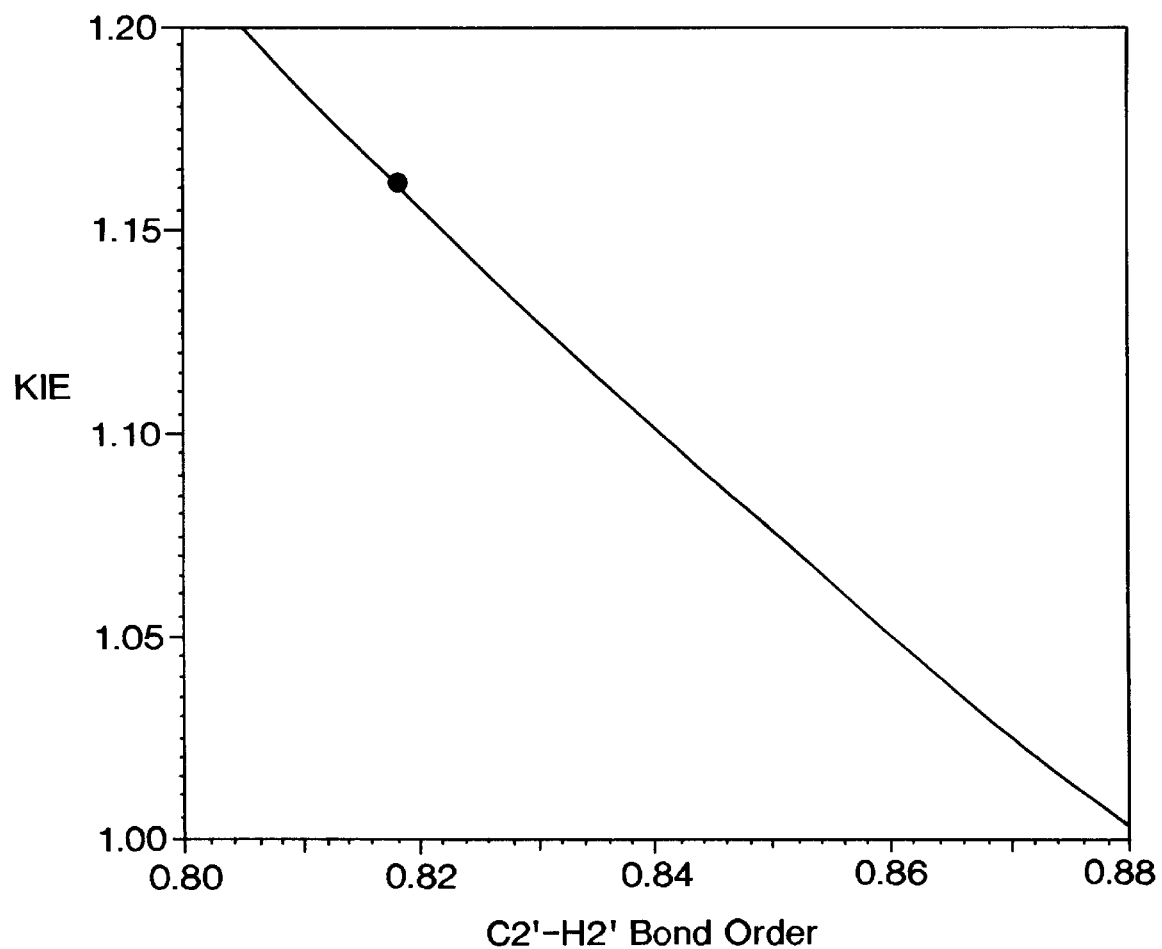
FIG. 7 represents the effect of altered C2'H2' bond order on the β-secondary $^3H$ kinetic isotope effect. The ordinate give the kinetic isotope effect for 2'-$^3H$ as the C2'-H2' bond order increases the solid line is calculated $^3H$ kinetic isotope effects from BEBOVIB-IV calculations.

The process of converging on a transition-state structure which was consistent with the experimental isotope effects was simplified by the observation that the calculated 2'-$^3$H isotope effect was only sensitive to variations in the C2'-H2' bond order when the dihedral angle between C2'-H2' and C1'-N9 is nearly eclipsed. The ribonolactone model of the transition state predicted that C2'-H2' would be nearly eclipsed with the C1'-N9 bond of the departing purine. All other isotope effects were independent of these variations. FIG. 7 shows the calculated 2'-$^3$H isotope effect as a function of C2'-H2' bond order and the experimental value. A bond order of 0.819±0.001 was found to agree with the experimental value. The uncertainty in the bond order reflects the standard error of 0.003 associated with the experimental measurement of the kinetic isotope effect. All subsequent calculations on transition states included this C2'-H2' bond order and the associated increase in bond order between C1'-C2' due to the hyperconjugative interaction.

Figure 6:
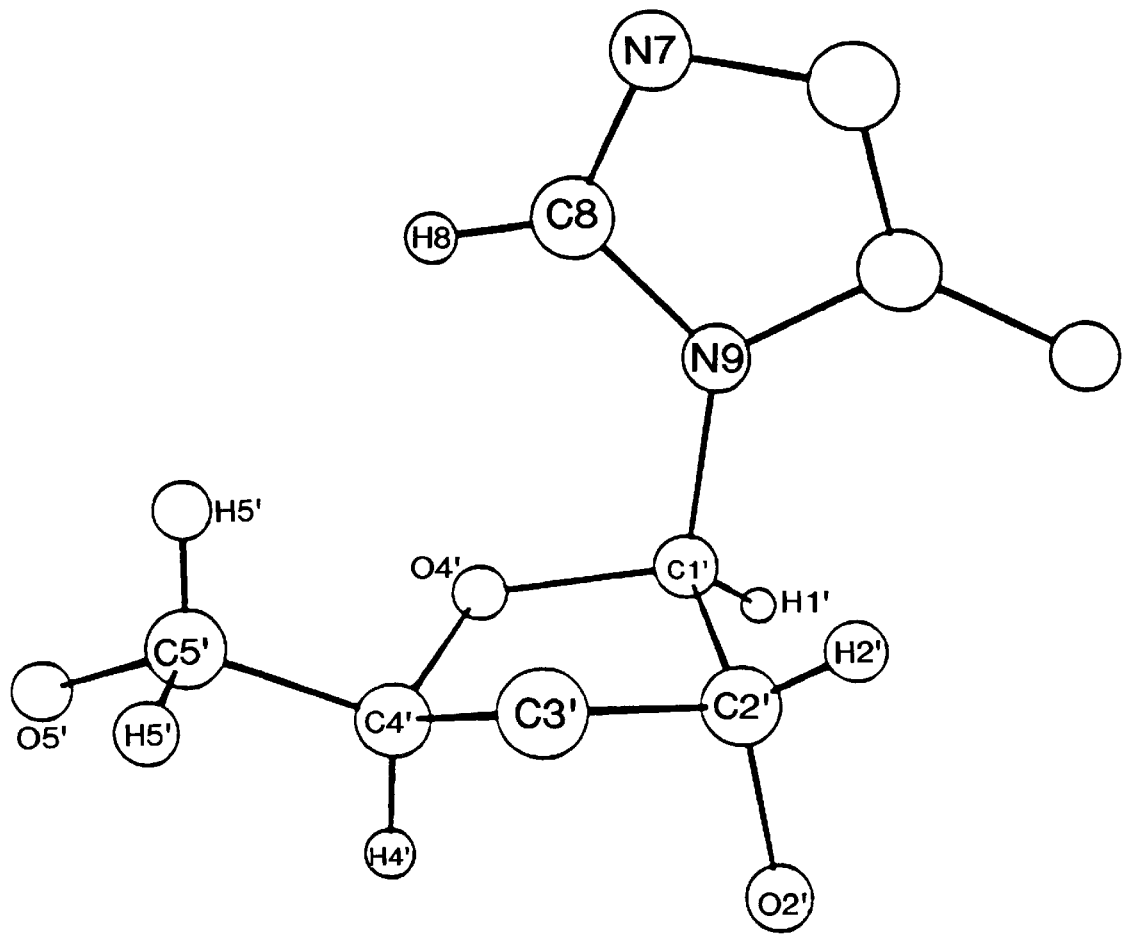
FIG. 6 represents the structure, nomenclature and bond lengths of the reactant inosine used in BEBOVIB calculations. On lengths for carbon-hydrogen bonds are from AMPAC calculations.
Figure 8:
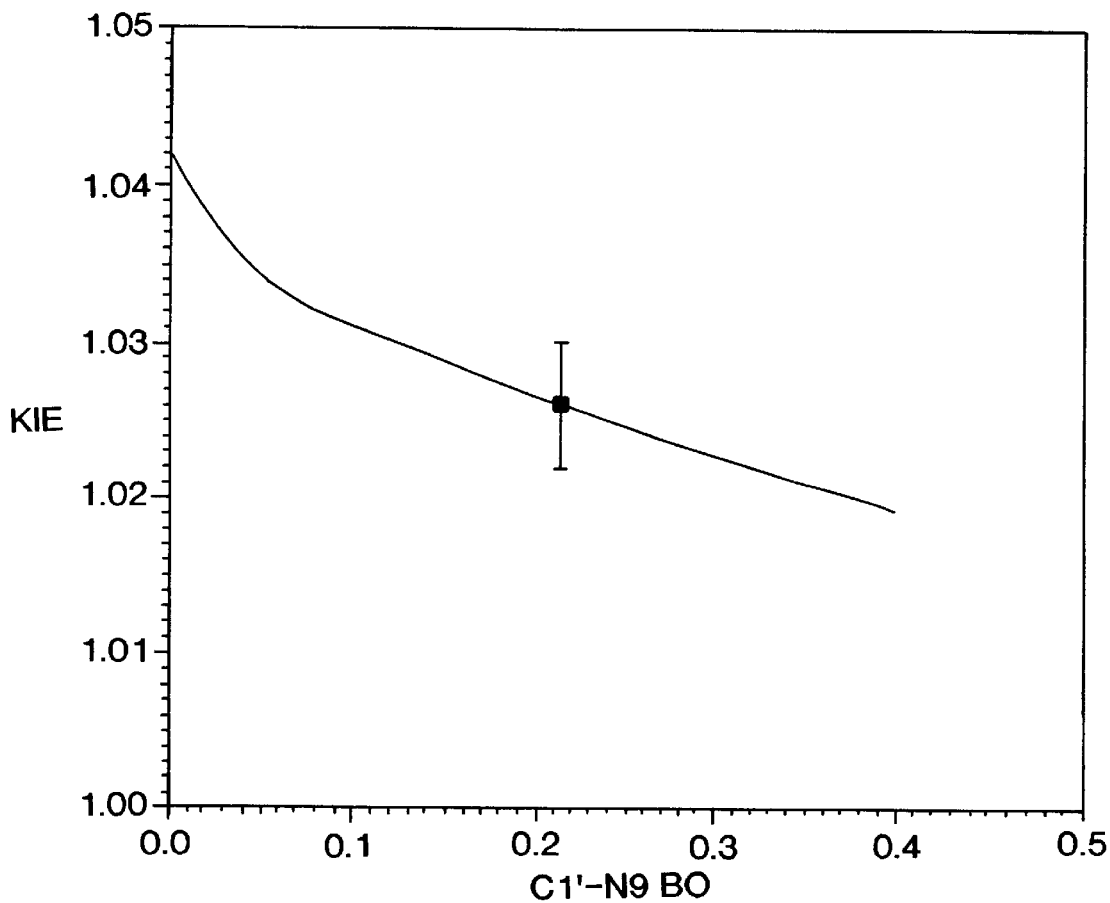
FIG. 8 represents the effect of altered C1'-N9 bond order on the $^{15}N$ kinetic isotope at N9. The solid line is the $^{15}N$ kinetic isotope effect for N9 calculated with the BEBOVIB-IV routine as a function of the C1'-N9 bond order. The experimental points and associated standard errors indicate the C1'-N9 bond order which is consistent with the experimental data.

The 9-$^{15}$N kinetic isotope effect is a function of the bond order between C1'-N9 and the electron distribution between the N9-C8 and C8-N7 bonds of the hypoxanthine residue (see FIG. 6). The relationship between the bond order of the breaking C1'-N9 bond, the calculated 9-$^{15}$N kinetic isotope effect, and the experimentally determined value are illustrated in FIG. 8. A 9-$^{15}$N kinetic isotope effect of 1.026±0.004 requires a C1'-N9 bond order of 0.22±0.1. The uncertainty of the C1'-N9 bond order is based on the error in the experimental measurement and is illustrated in FIG. 8. The magnitude of the 9-$^{15}$N isotope effect rules out transition states with C1'-N9 bonds below 0.1 bond order.

Figure 9:
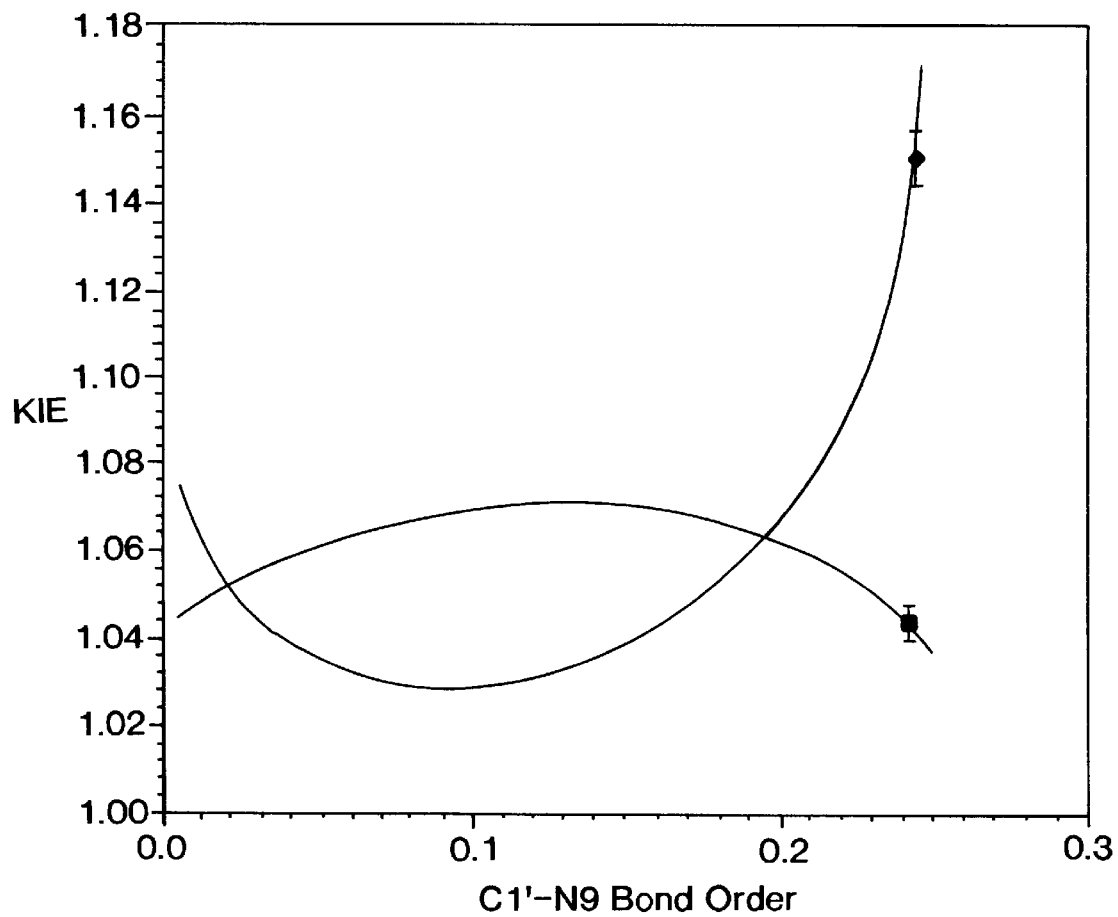
FIG. 9 represents and example of the effect of the C1'-N9 bond order on the calculated 1'-$^3H$ and 1'-$^{14}C$ kinetic isotope effects. The solid curves are calculated isotope effects while the experimental 1'-$^3H$ and 1'-$^{14}$ kinetic isotope effects are shown as the data points together with the associated experimental error. The concave-up curve is for the 1'-$^3H$ isotope effect, and the concave-down curve is for the 1'-$^{14}C$ isotope effect. The C1'-N9 bond order consistent with the experimental data is 0.248.

Kinetic isotope effects were also calculated for transition-state families in which the C1'-O4' bond order of the oxocarbonium intermediate was fixed and the C1'-N9' and C1'-O' bond orders were varied in order to match the 1'-$^{14}$C and 1'-$^3$H kinetic isotope effects. FIG. 9 shows an example of this approach. Any C1'-N9 and C1'-O' bond orders which did not simultaneously match the experimental kinetic isotope effects were eliminated. This approach established a transition-state structure having a C1'-N9 bond order of 0.225±0.095 and is consistent with the data obtained from the 9-$^{15}$N isotope effect. The partial bond to the leaving group in the transition state indicated that the geometry at C1' would not be completely rehybridized to sp$^2$ as expected for a pure $S_N1$ reaction. The following equation was used to describe the extent of rehybridization in the transition state:

$$a=90°+19.5° \text{ (C1'-N9 bonding)}$$

where a is the angle described by N9, C1' and any one of the three atoms attached to C1' and C1'-N9 bonding is defined as (C1'-N9 bond order in the transition state)/(C1'-N9 bond order in the reactant state).

The geometry of C1' was adjusted for partial bond formation between C1'-N9 in the transition state using this equation and the new structure analyzed by BEBOVIB calculations to determine the effect of the hybridization geometry on the calculated kinetic isotope effects. Only the 1'-$^3$H kinetic isotope effect was sensitive to change in a. Small changes in bond order between O' and C1' were then sufficient to produce agreement with the experimentally determined isotope effects.

Figure 10:
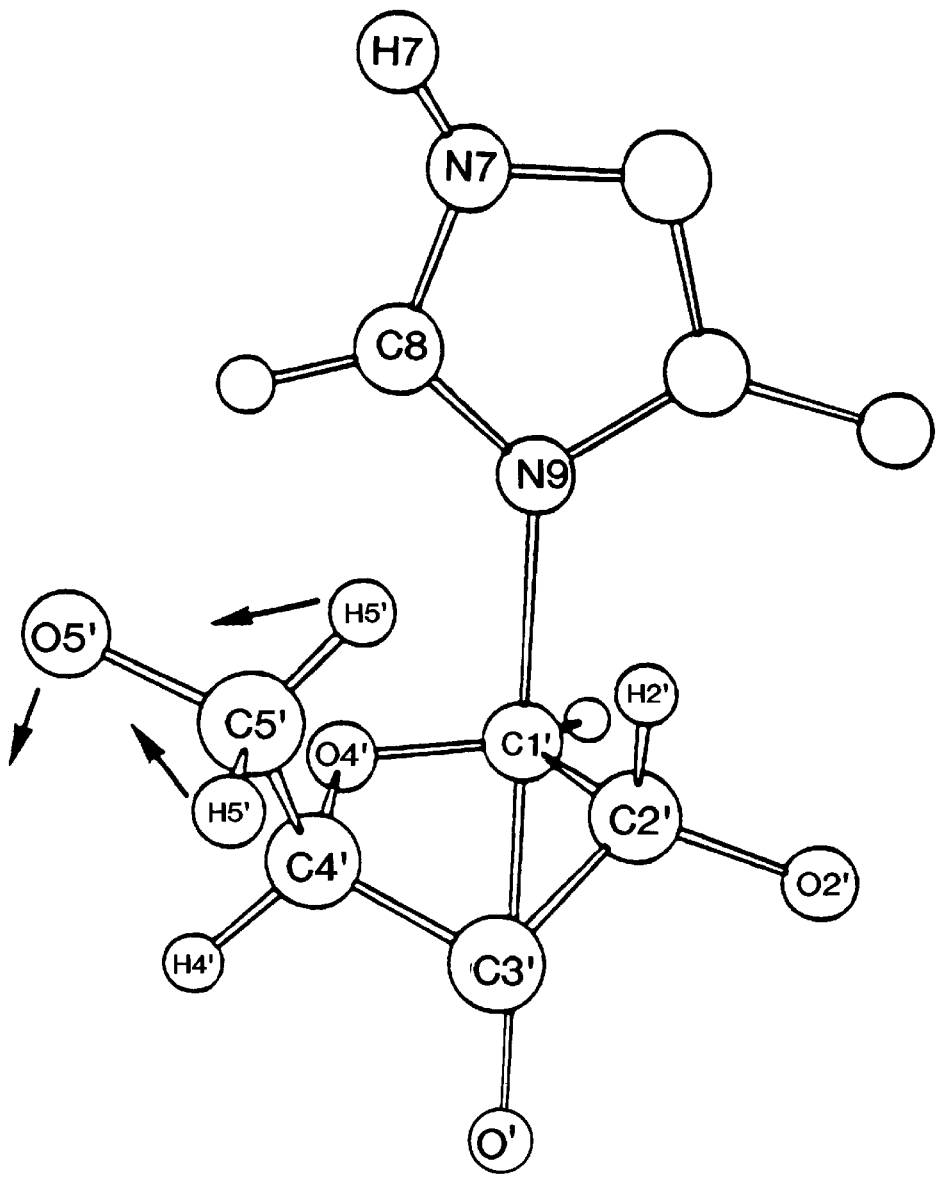
FIG. 10 represents the transition state for a nucleoside hydrolase. The structure is in agreement with the family of kinetic isotope effects shown in Table IV.

The transition-state structure which is consistent with the experimental kinetic isotope effects is shown in FIG. 10. The error limits on each of the bonds relates to the uncertainty in the experimental measurement of the kinetic isotope effects summarized in Table IV. The transition state had substantial oxocarbonium ion character with the C1'-N9 glycosidic linkage nearly broken while the attacking oxygen nucleophile had very low bond development. The transition state bond length between O4' and C1' was decreased substantially from 1.417 to 1.30±0.05 A, reflecting the oxocarbonium ion character of the transition state. The bond length at H2' was increased from 1.128 to 1.160 A to reflect the hyperconjugative interaction with C1' as described above.

The intrinsic nature of the isotope effects was demonstrated by a combination of steady-state kinetic properties and the magnitude of the isotope effects. A rapid-equilibrium random mechanism for substrate addition and product dissociation was established. This mechanism revealed that dissociation of products and substrate from the enzyme was much faster than conversion of inosine to products. This can only occur with a low commitment to catalysis and is consistent with the observation of intrinsic kinetic isotope effects. The $V_{max}/K_m$ value for inosine is $7.6 \times 10^{-4}$ M$^{-1}$ S$^{-1}$, well below the level of $10^8$–$10^9$ expected if every enzyme-inosine interaction resulted in product formation. The 1'- and 2'-$^3$H kinetic isotope effects were similar in magnitude to those found for the acid-catalyzed reaction. The presence of a significant commitment to catalysis would result in lower values for these isotope effects. The kinetic isotope effect for [1'-$^3$H]adenosine was measured under the same conditions and gave the same value as for the [1'-$^3$H]inosine experiment. Since $V_{max}/K_m$ for inosine is 7.8 times greater than that for adenosine, any significant commitment would be expected to result in a lowered experimental kinetic isotope effect with inosine as the substrate. When intrinsic or near-intrinsic isotope effects are observed, the results provide direct information on the nature of the transition state.

In terms of qualitative transition-state analysis, the isotope effects indicated that nucleoside hydrolase stabilizes an $S_N1$-like transition state which contains substantial oxocarbonium ion character. Strong hyperconjugative interactions were implicated by the magnitude of the β-secondary isotope effect. The a-secondary isotope effect predicted a ribosyl oxocarbonium ion with near sp$^2$ hybridization at C1'. Ribonolactone was used as the model compound for the transition-state analysis, on the basis of its known structure and its planarity at C1'. The bond order at H1' of the transition-state structure for nucleoside hydrolase was increased slightly by 3.4% in order to reflect the sp$^2$ hybridization at C1'. The structural model for the departing hypoxanthine was an imidazole residue which was protonated at the N distal from the glycosidic linkage (equivalent to N7 of inosine). Without protonation, hypoxanthine would be a poor anionic leaving group. The acid-catalyzed solvolysis of inosine has been proposed to proceed largely through a monoprotonated hypoxanthine cation. The small solvent deuterium kinetic isotope effect of 1.30 indicated nearly complete transfer of at least one proton in the transition state. A proton in flight at the transition state, midway between donor and the N7 of hypoxanthine, would be expected to give an isotope effect near 6. Additional evidence of N7 protonation comes from the lack of substrate activity of tubercidin (7-deazadenosine), which lacks N7. Finally, the value of the observed $^{15}$N kinetic isotope effect requires bond orders to N9 that can only be rationalized in the presence of protonation at N7. The combination of these features provided the qualitative features for the transition-state structure. Quantitative analysis of the transition state used these features as starting points and refined the structure to match the kinetic isotope effects predicted by BEBOVIB-IV.

$S_N1$ reaction coordinates which involved dissociation of the C1'-N9 bond without participation of the O' nucleophile (see FIG. 10) gave calculated 9-$^{15}$N isotope effects which were greater than the experimental value. Similar results were obtained when the attacking O' was included in the vibrational model but was not coupled to C1'-N9 vibration. Only reaction coordinates which involved coupling of C1'-O' motion with C1'-N9 motion provided calculated isotope effects which agreed with the experimental values.

The 1'-$^3$H kinetic isotope effect of 1.150 is approaching the value of 1.23 observed for the acid-catalyzed hydrolysis of inosine. The unusually large value of 1.161 for the 2'-$^3$H kinetic isotope effect is diagnostic for the presence of hyperconjugation to C2' in the transition state and simultaneously rules out an $S_N2$ displacement at C1'. The 2'-$^2$H kinetic isotope effect for the acid-catalyzed hydrolysis of adenosine 5'-monophosphate is 1.077, and use of the Swain-Schaad relationship predicts a $^3$H kinetic isotope effect of 1.113. Since the β-secondary isotope effect seen for the nucleoside hydrolase reaction was larger than that found for chemical solvolysis, it was apparent that H2' underwent interactions on the enzyme which do not occur in solution. An explanation for the magnitude of the kinetic isotope effect is a ribosyl conformation in the active site which fixes the dihedral angle described by H2'-C2' and C1'-N9 at or near 0°. This interaction maximizes hyperconjugative interaction. In solution, this conformation could be one in a population of reactive conformations, some of which would not give rise to the maximum β-secondary kinetic isotope effect. On the enzyme, specific interaction of an active site residue(s) such as a carboxylate with the oxocarbonium ion could position the transition state at a location on the reaction coordinate which undergoes more hyperconjugation than in solution. Finally, hydrogen bonding to the 2'OH could stabilize the oxocarbonium ion through inductive effects. The increase in electron density would result in lengthening of the C2'-H2' bond, contributing to the observed isotope effect due to greater vibrational freedom of H2'. Interaction of enzymatic groups with the 2'-hydroxyl was also indicated by the substrate specificity of nucleoside hydrolase, where 2'-deoxynucleosides were poor or inactive as substrates. The attacking water could have only very low bond formation to C1'. Any O'-C1' bond order above 0.019 caused the calculated 1'-$^3$H isotope effect to disagree with the experimental results. In the transition state, water is poised to trap the oxocarbonium ion but has little involvement in the cleavage of the glycosidic bond. It is unclear whether water or hydroxide is the attacking species since O'-C1' bond formation is so weak at the transition state. At some point in the reaction coordinate, it is necessary for the attack to be completed by the hydroxyl as O'-C1' bond formation occurs.

The attacking oxygen nucleophile was a specific water-derived ligand which has been activated by the enzyme. Attack of a general solvent nucleophile on an enzyme-stabilized oxocarbonium has been ruled out by demonstrating that methanol cannot attack the oxocarbonium to yield 1-methylriboside as product. Enzymes which permit attack on oxocarbonium-like intermediates readily form the products expected by methanol attack.

The primary $1'$-$^{14}$C isotope effect was in the range expected for an $S_N1$-like transition state. Its occurrence was an indication of less restricted motion at C1' in the transition state relative to the ground state, consistent with an $S_N1$-like or highly expanded $S_N2$-like process. A symmetric $S_N2$ transition state around C1' would cause a primary $1'$-$^{14}$C isotope effect around 1.10, considerably outside the observed range.

Loss of full bond to N9 in the transition state predicted an isotope effect near 1.04. The intermediate value of 1.026 observed for the 9-$^{15}$N kinetic isotope effect required a transition state having sufficient bond order at N9 to suppress the isotope effect. The C1'-N9 glycosidic bond order could not be increased beyond 0.32 since this caused a decrease in the calculated $1'$-$^3$H and $^{14}$C kinetic isotope effects below the experimental values. The alternative was to protonate N7, which had the effect of increasing bond order at N9 due to resonance. A proton was required chemically in the reaction mechanism and served as an acid catalyst to destabilize the glycosidic linkage by introduction of a positive charge. The combined solvent and substrate kinetic isotope effects made it likely that in the transition state a proton donor had completed or nearly completed transfer of a proton to N7. The sum of bond order in the hypoxanthine ring was greater in the transition state that in the reactant state, requiring the presence of a partial positive charge in the ring at the transition state.

The large isotope effect for the 5-$^3$H of inosine was surprising, being four bonds removed from the site of bond breaking and formation. Indeed, the AMP nucleosidases showed $5'$-$^3$H kinetic isotope effects near unity, consistent with similar structures for the reactant and transition states at the 5'-carbon of AMP. In contrast, the nucleoside hydrolase transition state differed substantially from those found for the AMP nucleosidases. This difference indicated an enzyme-induced distortion at the 5'-carbon in the transition state.

Since the $5'$-$^3$H isotope effect for nucleoside hydrolase was normal (i.e., >1.0), the C5'-H5' bond experienced a net loosening in the transition state relative to inosine in solution.

This could be realized by decreasing the C5'-H5' bond order or by placing H5' in a less crowded environment in the transition state. BEBOVIB calculations revealed that the $5'$-$^3$H isotope effect may arise from changes in any of the three angle-bending modes involving H5' or from decreases in the bond orders of any of the bonds within two atoms of H5'. Factors which could effect this change in bond order include a long-range electronic interaction of H5' with the oxocarbonium ion, hydrogen bonding of the O5' hydroxylic hydrogen to either the enzyme or the substrate itself, or a flattening of the sp$^3$ hybridization at C5'. AMPAC modeling indicated that the C4'-O4' bond was lengthened due to the adjacent oxocarbonium ion. Decrease in the C4'-O4' bond order arises from a resonance contributor of the oxocarbonium ion in which C4'-O4' bond decrease contributes the electron pair to oxygen with a developing positive charge on C4'. An aligned C5'-H5' bond could hyperconjugate with the developing positive charge at C4'. Further theoretical and experimental observations are necessary to more filly predict the isotope effects which arise from these interactions.

AMPAC calculations on ethanol suggested that a hydrogen bond from the 5'-hydroxyl to an acceptor would cause an increased in the H5'-C5' bond length and a decrease in the length of the C5'-O5' bond. These two changes would result in small normal and inverse isotope effects, respectively, but they effectively cancel one another. Thus, simple, in-line hydrogen bonding is unlikely. Alternatively, the 5'-hydroxyl could serve as a lever through which the substrate is held in a reactive conformation to result in a flattening or distortion of the hydroxymethyl group. BEBOVIB calculations indicate that a 3° change in bond angles at the hydroxymethyl group in the directions shown in FIG. 10 would result in a $5'$-$^3$H isotope effect of 1.05. An interaction with the hydroxymethyl group sufficient to result in its distortion is also likely to stiffen the O5'-C5'-H5' bending mode. Increase in the angle-bending force constant by 10% resulted in an inverse isotope effect of 0.96, demonstrating that simple "anchoring" of the hydroxymethyl group cannot be the sole source of the $5'$-$^3$H isotope effect. Changes in force constants could nonetheless play a role in contributing to the observed isotope effect by acting to reduce the magnitude of a normal isotope effect which arises due to flattening of the hydroxymethyl group. It has been shown that 5'-deoxynucleosides are not substrates for nucleoside hydrolase, yet they are inhibitors with $K_i$ values approximately double the $K_m$ for the corresponding substrates. These results, together with the kinetic isotope effects, implicate a transition-state function for the 5'-hydroxyl. A hydrogen bond from the protein to the 5'-hydroxyl could serve as a lever which orients the substrate in a reactive conformation, distorts the geometry at C5', and gives the observed isotope effect. Until the validity of long-range electronic interaction between H5' and the oxocarbonium can be evaluated, the preferred interpretation of the $5'$-$^3$H isotope effect is from binding distortion which occurs in the transition state.

The inverse 4-$^3$H kinetic isotope effect is consistent with an increased bond order at C4'-H4' in the transition state or a more restricted environment. BEBOVIB modeling indicated that the isotope effect is sensitive to changes in bond stretches and/or bond angle bends in which H4' is involved. The sp$^2$ hybridization at C1' in the transition state results in changes in the bond lengths of the ribose ring atoms, which in turn perturb the angle-bending modes involving H4'. Another contribution to the observed 4'-$^3$H kinetic isotope effect might be a change of the H4'-C4'-O4' force constant, due to the adjacent oxocarbonium ion. The small magnitude of this isotope effect and the several possible sources for it make the assignment of its origin uncertain. However, it is clear that long-range kinetic isotope effects are due to unique conformations and interactions which occur in the transition state.

Nucleoside hydrolase contains two active site anions having overlapping pK's near 6.1. The two groups are manifested in the $V_{max}$ and $V_{max}/K_m$ profiles but not in the $K_m$ profile and are therefore involved in transition-state interactions but not in substrate binding. The transition state deduced from isotope effects contains two regions of positive charge, one corresponding to the oxocarbonium ion and the other corresponding to the excess bond order in the departing hypoxanthine ring. It is possible that one or both of the anions (perhaps carboxylates) in the active site are responsible for transition-state stabilization through interaction with the positively charged regions of the transition state. A feature proposed for glycosidase catalysis is the carboxylate stabilization of carbocationic transition states.

In addition to these interactions, one addition group must be involved in the protonation at N7. Since this donor must be protonated to be functional, the $pK_a$ value for this group may be outside the range of the $pK_a$ profile experiment. Another group would be expected to accept the proton from $H_2O$ to form the attacking hydroxyl. It is possible that one of the groups with a pK value of 6.1 could be a proton acceptor for the enzyme-activated nucleophile.

The large isotope effects observed for the 2'-$^3$H and the remote 5'-$^3$H kinetic isotope effects argue for a transition state held in a reactive conformation by the enzyme. The importance of the 2'-, 3', and 5'-hydroxyls for catalysis suggests that the transition-state structure is oriented in part via hydrogen bonds to all hydroxyls of the ribose ring. The family of kinetic isotope effects reported here and the associated transition-state analysis indicate that it is possible to obtain complete conformational analysis of a transition state using an extension of these methods. Multiple remote isotope effects demonstrated the potential to allow for a precise definition of the ribose ring conformation in the transition state.

The combination of multiple heavy atom kinetic isotope effects and transition-state analysis provided a new approach toward inhibitor design. Transition states determined by this approach provide a snapshot of transition-state structure unavailable by X-ray crystallographic, NMR, or other static spectroscopic techniques. Incorporation of key transition state features in a stable, ground-state molecule provides specific enzyme inhibitors with high affinities for the target enzyme. The ideal inhibitor must match the transition state geometrically, electronically, and for H-bond ligands. The nucleoside hydrolase transition-state described here suggests inhibitors having the following properties: A C-nucleoside linkage would serve to mimic a lengthened glycosidic linkage and confer stability against hydrolysis. The oxocarbonium and aglycon positive charge should be represented by incorporation of positive charges into the inhibitor. The 9-$^{15}$N isotope effect indicates protonation at N7 in the transition state. A basic group or H-bond acceptor in the appropriate position of the inhibitor should enjoy the same interaction. Hydroxyl groups at the 2'-, 3'-, and 5'-positions of the ribose ring are also requisite functional groups, on the basis of the isotope effects and steady-state kinetic properties of the 2'- and 5'-deoxy-compounds. An analogue incorporating these features, as in the Example below, would be an exceptional inhibitor on the basis of the unique knowledge of transition-state structure available from kinetic isotope effects and transition-state analysis.

The transition state for nucleoside hydrolase can be described within narrow limits as a structure with well defined bond lengths and conformational properties. The transition state has substantial oxocarbonium ion character, a protonated leaving group, the glycosidic linkage largely cleaved, and an enzyme-directed attacking O nucleophile just within bonding distance but having low bond order to its target carbon. The ribose portion of the nucleoside is held in a reactive conformation via interactions with its hydroxyl groups. The observation of kinetic isotope effects remote from the site of bond breaking enables extension of the use of enzyme kinetic isotope effects to report on binding and/or conformational phenomena which are unique to enzymic transitions states. These results make it possible to deduce novel transition-state conformations by a combination of kinetic isotope effects and BEBOVIB analysis. This information provides a glimpse at the transition state not possible using only crystallographic or other spectroscopic approaches which examine ground-state populations. Transition-state structure can be applied to the design of transition-state analogue inhibitors which mimic electronic, geometric, and hydrogen-bonding transition-state features.

The phenyl iminoribitol may be synthesized by the addition of phenylmagnesium bromide to imine 3 (see Scheme 1 of FIG. 11), itself derived from the 1,4-dideoxy-1,4-imino-D-ribitol 4, affording the 1-(S)-phenyl iminoribitol 5. (Horenstein, B. A.; Zabinski, R. F.; Schramm, V. L. Tetrahedron Lett., 1993, 34, 7213–7216.) The iminoribitol 4 is accessible from D-gulonolactone via a rather lengthy nine step process (Horenstein, B. A.; Zabinski, R. F.; Schramm, V. L. Tetrahedron Lett., 1993, 34, 7213–7216, Fleet, G. W. I.; Son, J. C. Tetrahedron, 1988, 44, 2637–2647), but is nevertheless readily available on a multi-gram scale. The same imine 3 was utilized and treated with appropriate aryllithium or aryl Grignard reagents. An alternative approach has been recently reported (Yokoyama, M.; Akiba, T.; Ochiai, Y.; Momotake, A.; Togo, H. J. Org. Chem., 1996, 61, 6079–6082) which involves aryllithium addition to a 2,3,5-O-protected D-ribose, subsequent oxidation and then a double reductive amination.

Using 4-chlorophenylmegnesium bromide and 4-fluorophenyl magnesium bromide, the substituted phenyl iminoribitols 6 and 7 were obtained in 35% and 46% yield, respectively, from the iminoribitol 4. 1,4-Dibromobenzene was selectively monlithiated (BuLi, −78° C.) affording 4-bromophenyllithium which was allowed to react with imine 3 (THF, −78° C.) to give the bromophenyl derivative 8.

In order to prepare imine derivatives, 3- and 4-bromoanaline were separately N,N-diallylated and the products treated woth butyllithium, generating 3- and 4-N,N-diallylaminophenylllithium. These reagents were reacted in situ with imine 3 to give the protecetd aniline derivatives 9 and 10. Similarly, O-$^t$butyldiphenylsilyl-4-bromophenol was treated with butyllithium and the lithiated aromatic was allowed to react with imine 3 affording the protected phenol 11. Attempts to lithiate 3-bromopyridine by lithium-halogen exchange were unsuccessful at −78° C., but at −100° C. (THF, BuLi) the 3-lithiopyridine was generated, and on addition of imine 3 the pyridine 12 was obtained.

The 1-(S) stereochemistry of these adducts is assumed by analogy with the phenyl iminoribitol 5 which has been characterized by anaylsis of nOe's in its NMR spectrum (Horenstein, B. A.; Zabinski, R. F.; Schramm, V. L. Tetrahedron Lett., 1993, 34, 7213–7216).

The 4-bromophenyl imminoribitol 8 was treated with butyllithium (THF, −78° C.) resulting in lithium-bromine exchange and the resulting aryllithium species was quenched in situ by $CO_2$ affording carboxylic acid 13.

Figure 12:
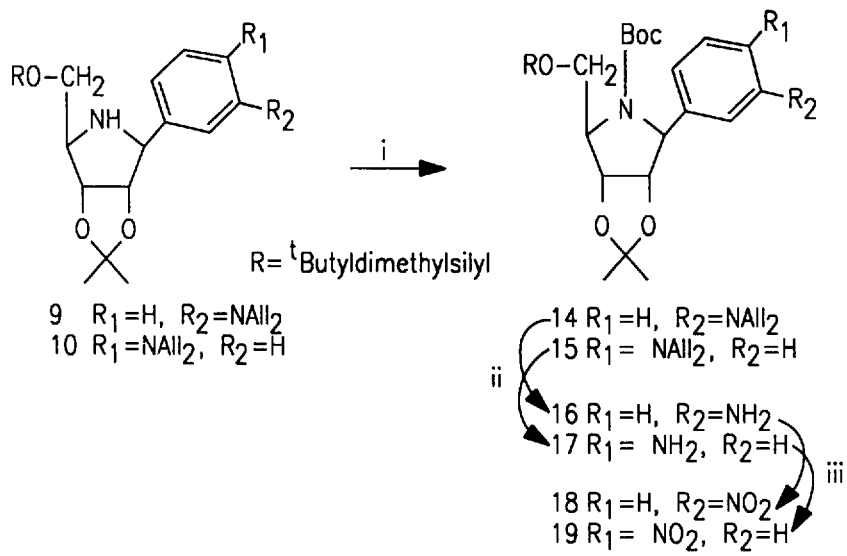
FIG. 12 sets forth a representation of scheme 2, a general scheme by which the coumpounds of the present invention may be prepared. Also shown are the products that are produced using this scheme.
Figure 12:
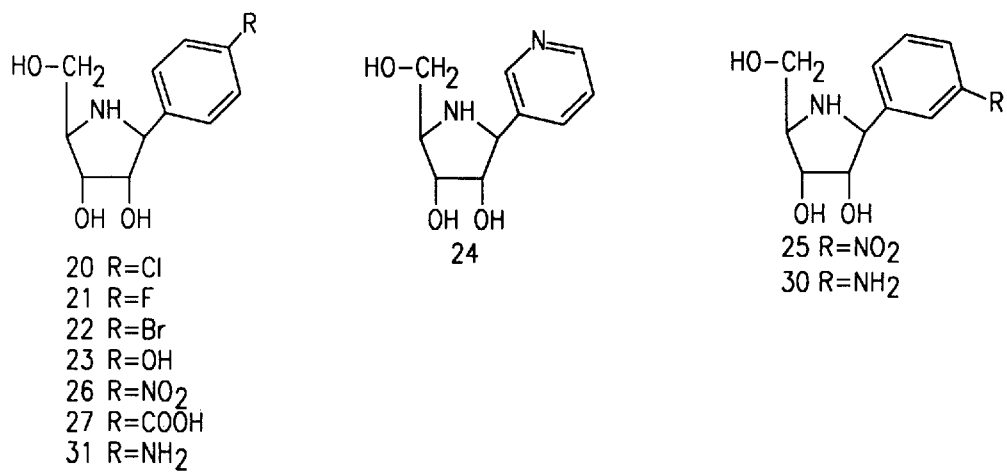

In order to prepare nirophenyl derivatives, the anilines 9 and 10 were converted into $^t$butyl carbamates 14 and 15 (see Scheme 2 of FIG. 12) followed by de-N-allylation using Wilkenson's catalyst (Laguzza, B. C.; Granem, B. Tetrahedron Lett., 1981, 22, 1483–1486). The resulting amines 16 and 17 were oxidized using oxone® (potassium peroxymonosulfate) (Webb, K. S.; Seneviratue, V. Tetrahedron Lett., 1995, 36, 2377–2378) affording the nitrophenyl iminoribitols 18 and 19.

Deprotection of compounds 6–8, 11, 12, 18 and 19 was achieved by acid hydrolysis followed by neutralization of the product salts with base resin. This afforded the 1,4dideoxy-1,4-imino-1-(S)-substituted phenyl)-D-ribitols 20–26. The carboxylic acid 27 was obtained as the ammonium salt by acid hydrolysis of 13 followed by elution from acid resin with aqueous ammonia. Analines 9 and 10 were first de-N-allylated using Wilkenson's catalyst to give 28 and 29 which were then subjected to acid hydrolysis followed by neutralization with base resin affording the aminophenyl iminoribitols 30 and 31.

The phenyl iminoribitol derivatives 20–27, 30 and 31 provide useful information on the structure-activity requirements for inhibition of nucleoside hydrolases and to further extend understanding of the nature of the transiton state of other N-ribosyl hydrolases and transferases.

Example 1

Synthesis of (2S)-phenyl(3S, 4R)-dihydroxy-(5R)-hydroxymethyl-pyrrolidine.

The following ingredients, which are all commercially available, were used to synthesis the compound (2S)-phenyl (3S,4R)-dihydroxy-(5R)-hydroxymethyl-pyrrolidine:

N-benzyl-2,3-isopropylidine-1,4-dideoxy-1,4-imino-D-ribitol
dichloromethane
t-butyl-dimethylsilyl chloride
triethylamine
4-(N,N-dimethyl-amino)-pyridine
diethyl ether
sodium sulfate
silica gel
hexanes
ethyl acetate
10% Pd—C
ethanol
hydrogen gas
pentane
N-chloro-succinimide
tetrahydrofuran
n-butyl lithium
diisopropyl amine
sodium bicarbonate
sodium chloride
trimethylsilyl triflate
phenyl lithium
trifluoroacetic acid
water This compound has the formula:

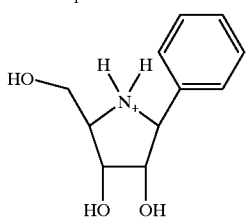

Example 2

Synthesis of (2S)-phenyl-(3S,4R)-dihydroxy-(5R)-hydroxymethyl-pyrrolidine

The compound (2S)-phenyl-(3S,4R)-dihydroxy-(5R)-hydroxymethyl-pyrrolidine was synthesized as follows:

1. Preparation of 5-t-butyl-dimethylsilyl-N-benzyl-2,3-isopropylidine-1,4-dideoxy-14-imino-D-ribitol N-benzyl-2,3-isopropylidine-1,4-dideoxy-1,4-iminoD-ribitol, prepared by the method described in Fleet, et al., *Tetrahedron*, Vol. 44, pages 2637–2647 (1988). 0.33 g, 1.25 mmol was dissolved in 2.0 mL of dichloromethane and reacted with t-butyl-dimethylsilyl chloride (0.226 g, 1.5 mmol) in the presence of triethylamine (0.226 mL, 1.63 mmol) and a catalytic amount of 4-(N,N-dimethyl-amino) pyridine (0.15 g). After stirring 22 hours at room temperature, the reaction mixture was diluted with 25 mL of diethyl ether and the resulting triethylammonium chloride was removed by filtration. The ethereal solution was washed with 20 mL of distilled water, and then with 20 mL of saturated NaCl solution. The ethereal solution was dried over $Na_2SO_4$. Column chromatography on silica gel in 4:1 hexanes/ethyl acetate afforded 0.400 g (85% yield) of 5-t-butyl-dimethylsilyl-N-benzyl-2, 3-isopropylidine-1,4-imino-D-ribitol as a pale green oil.

Example 3

Preparation of 5-t-butyl-dimethylsilyl-2,3-isopropylidine-1,4-dideoxy-1,4-imino-D-ribitol 5-t-butyl-dimethylsilyl-N-benzyl-2,3-isopropylidine-1, 4dideoxy-1,4-imino-D-ribitol (0.399 g, 1.06 mmol) and 50 mg of 10% Pd-C were stirred in 5.0 mL of ethanol under hydrogen gas at 1 atm for 14 hours. The Pd-C was removed by filtration through Celite. TLC analysis (silica, 4:1 hexanes/ethyl acetate) indicated complete conversion of starting material to product ($R_f$=0.57) with no side products observed. Concentration provided 0.294 g (97% yield) of 5-t-butyl-dimethylsilyl-2,3-isopropylidine-1,4-dideoxy-1,4-imino-D-ribitol, used without further purification.

Example 4

Preparation of 5-t-butyl-dimethylsilyl-N-chloro-2,3-isopropylidine-1,4-dideoxy-1,4imino-D-ribitol 5-t-butyl-dimethylsilyl-2,3-isopropylidine-1,4-dideoxy-1,4-dideoxy-1,4-imino-D-ribitol (0.293 g, 1.02 mmol) was dissolved in ca. 25 mL of dry pentane and stirred for 1 hour at room temperature with N-chloro-succinimide (0.164 g, 1.23 mmol). The white solids were removed by filtration through glass wool. TLC analysis showed clean conversion of amine to product (silica, 4:1 hexanes/ethyl acetate, $R_f$=0.68). The unstable N-chlorinated product was used immediately in the next step of the synthesis.

Example 5

Preparation of 5-t-butyl-dimethylsilyl-$W^{N,1}$ 2-dehydro-2,3-isopropylidine-1,4-dideoxy-1,4-imino-D-ribitol A 0.58 mM solution of lithium diisopropyl amide in THF was prepared from 1.00 mL of 1.9 M n-BuLi in hexane and 0.280 mL of dry diisopropylamine (2.0 mmol) in 2.0 mL of THF at −78° C.

5-t-butyl-dimethylsilyl-N-chloro-2,3-isopropylidine-1,4-dideoxy-1,4-imino-D-ribitol, prepared in the previous step, was dissolved in 1.0 mL of dry THF and cooled to −78° C., under Ar. LDA (1.72 mL, 1.00 mmol) was added dropwise over 15 minutes to the N-chloro compound. The reaction mixture was stirred 15 minutes at −78° C.; TLC analysis indicated complete loss of starting material. Quenching was performed by addition of 10 mL saturated aqueous $NaHCO_3$. After removal of THF in vacuo, the mixture was extracted with two 15 mL portions of ethyl acetate. The combined ethyl acetate extracts were washed with 15 mL saturated aqueous NaCl and dried over $Na_2SO_4$. Pure product was obtained as a yellow oil by column chromatography (silica, 3:1 hexanes/ethyl acetate); 0.078 g (27% yield). TLC: (3:1 hexanes/ethyl acetate, $R_f$=0.50).

Example 6

Preparation of (2S)-pheynyl-(3S,4R)-dihydroxy 3,4-isopropylidine-(5R)-t-butyl-dimethylsilyloxymethyl-pyrrolidine 5-t-butyl-dimethylsilyl-$W^{N,1}$dehydro-2,3-isopropylidine-1,4-dideoxy-1,4-imino-D-ribitol (0.039 g, 0.137 mmol) was dissolved in 1.0 mL of dry THF and cooled to 0° C. under Ar. Trimethylsilyl triflate (0.029 mL, 0.151 mmol) was added to the cooled solution, and stirring was continued for 30 minutes at 0° C. Phenyl lithium (1.5N/Et$_2$O, 0.164 mmol) was added dropwise, and the mixture warmed to room temperature by stirring. TLC analysis indicated substantial amounts of unreacted starting material. An additional aliquot of phenyl lithium was added (0.218 mL, 0.328 mmol) and the reaction continued for ca 18 hours at room temperature. The reaction mixture was diluted with 20 mL Et$_2$O, and partitioned against 20 mL of saturated NaHCO$_3$. The organic layer was washed with an additional 20 mL of saturated NaHCO$_3$, and then with 20 mL of saturated aqueous NaCl, and dried over Na$_2$SO$_4$. Purification by column chromatography on silica with a step gradient of hexanes/ethyl acetate in a ratio of 7:1 to 1:2 obtained 0.0107 g (22% yield) of (2S)-phenyl-(3S,4R)-dihydroxy-3,4-isopropylidine-(5R)-t-butyl-idemthylsilyloxymethyl-pyrrolidine. TLC: (5:1 hexanes/ethyl acetate, R$_f$=0.68).

Example 7

Preparation of (2S)-phenyl-(3S,4R)-dihydroxy(5R)-hydroxymethyl-pyrrolidine (2S)-phenyl-(3S,4R)-dihydroxy-3,4-isopropylidine-(5R)-t-butyl-dimethylsilyloxy methyl-pyrrolidine (0.0080 g, 0.022 mmol) was dissolved in 1.0 mL of 50% aqueous trifluoroacetic acid, and stirred at room temperature for 18 hours. The reaction mixture was concentrated in vacuo to dryness, and then suspended in 0.5 mL of distilled H$_2$O and reconcentrated. The residue was dissolved in 1.0 mL of distilled H$_2$O, and extracted with 1.0 mL of hexanes. The aqueous solution was concentrated to dryness, providing 0.0044 g (62% yield) of (2S)-phenyl-(3S,4R)-dihydroxy-(5R)-hydroxymethyl-pyrrolidine.

The compound (2S)-pheynyl-(3S,4R)-dihydroxy-(5R)-hydroxymethylpyrrolidine inhibits nucleoside hydrolase from *Crithidia fasciculata* with an inhibition constant of 0.15 mM, binding approximately 2,000-fold better than the substrate inosine. In order to determine the inhibition of nucleoside hydrolase by the synthesized (2S)-phenyl-(3S,4R)-dihydroxy-(5R)-hydroxymethyl-pyrrolidine compound, an assay of nucleoside hydrolase activity was performed by monitoring the decrease in absorbtion at 280 nm that occurs upon hydrolysis of the substrate inosine to the products hypoxanthine and ribose. All assays were performed at 30° C. in 50 mM bis-tris buffer at pH 7.3. The substrate for all assays was inosine. Inhibition studies were performed by examining the initial velocity of the hydrolysis of inosine as a function of inosine concentration and (2S)-phenyl-(3S,4R)-dihydroxy-(5R)-hydroxymethylpyrrolidine concentration. A total of 75 velocity measurements were made.

The general protocol for measurement was as follows: various concentrations of inosine and inhibitor in the above buffer were prepared, and 1.0 mL aliquots placed in a quartz cuvette and equilibrated at 30° C. The reaction was initiated by addition of nucleoside hydrolase (20–30 micrograms). The decrease in absorption at 280 nm was monitored over a 10 minute period. Initial velocity data were fit to the equation for competitive inhibition. Inhibitor (2S)-phenyl-(3S,4R)-dihydroxy-(5R)-hydroxymethyl-pyrrolidine inhibited nucleoside hydrolase with a K$_i$ of 0.150±0.015 micromolar.

(2S)-phenyl-(3S,4R)-dihyroxy-(5R)-hydroxymethylpyrrolidine is a transition state analog for the hydrolytic reaction catalyzed by nucleoside hydrolase, and is an extremely potent inhibitor of the enzyme. Steady state kinetic studies have established that the inhibition constant, K$_i$ for the inhibitor is 0.150±0.015 micromolar. This shows a competitive inhibition pattern, as expected for a transition state analog.

Example 8

Synthesis of Transition State Inhibitors for N-Riboside Hydrolases and Transferases N.m.r. spectra were recorded on a Bruker AC-300 instrument at 300 MHz or 75 MHz ($^{13}$C). In solvents other than D$_2$O$_3$ internal TMS was used as a reference. High resolution accurate mass determinations were performed on a VG70-250S mass spectrometer under chemical ionization conditions using isobutane or ammonia as the ionizing gas. Melting points were determined on a Reichert hot stage microscrope and are uncorrected. Aluminum backed silica gel sheets (Merck or Reidel de Haen) were used for thin layer chromatography. Column chromatography was performed on silica gel (230–400 mesh. Merck). Optical rotations were measure on a Perkin Elmer 241 polarimeter. Chromatography solvents were distilled prior to use.

Figure 11:
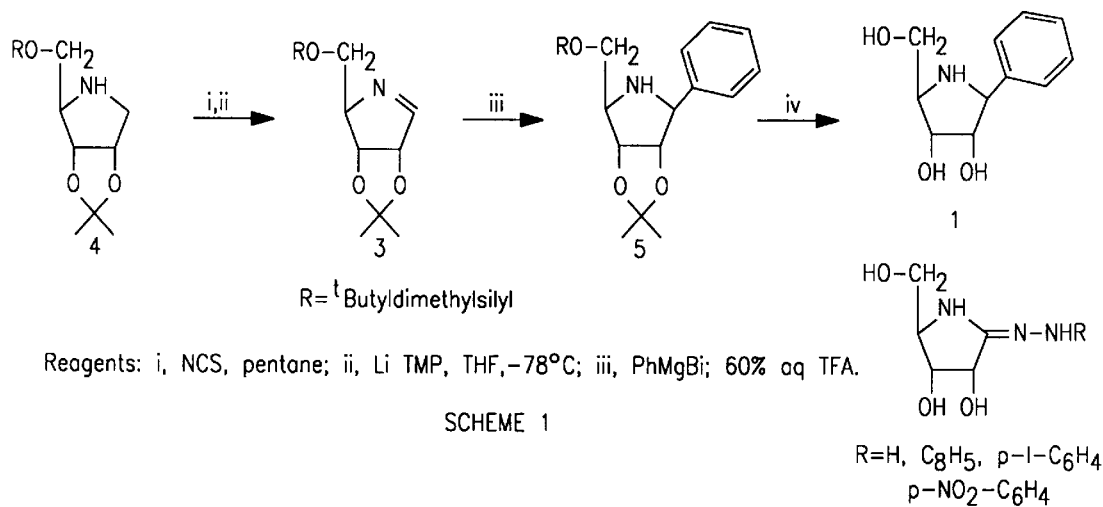
FIG. 11 sets forth a representation of scheme 1, a general scheme by which the coumpounds of the present invention may be prepared. Also shown are the products that are produced using this scheme.
Figure 11:
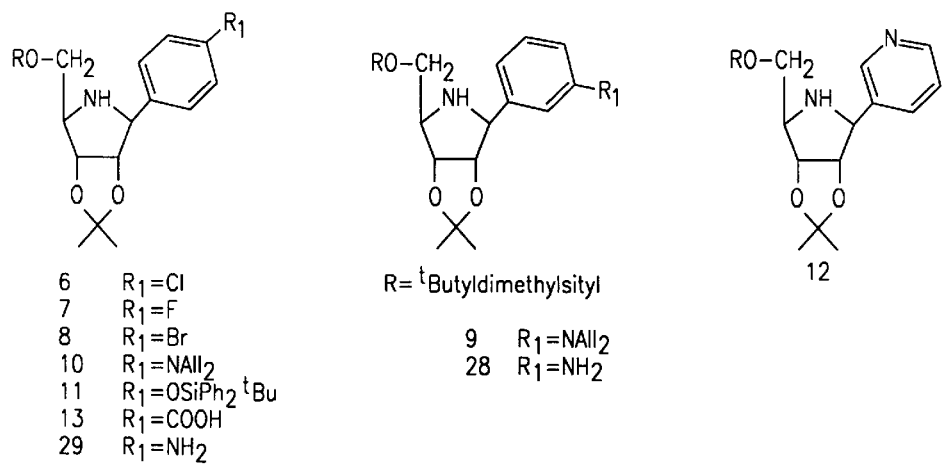

Synthesis of 5-O-$^t$Butyldimethylsilyl-1,N-dehydro-1,4-dideoxy-1,4-imino-2,3-O-isopropylidene-D-ribitol (see (3) in FIG. 11).

A solution of 5-O-$^t$butyldimethylsilyl-1,4-dideoxy-1,4-imino-2,3-O-isopropylidene-D-ribitol 4 in pentane (15 ml/mmol.) was treated with N-chlorosuccinimide (1.3 equiv.) and the mixture was stirred at room temperature until complete conversion of the amine to the corresponding N-chloro compound as judged by t.l.c. (ethyl acetate: petroleum ether 1:4) (usually –30 min.). The solids and solvent were removed and the residue was dissolved in dry tetrahydrofuran (15 ml/mmol.) and the solution was cooled to –78° C. A solution of 2,2,6,6-tetramethylpiperidine (1.5 equiv.) in dry tetrahydrofuran (5 ml/mmol.), previously treated with butyllithium (1.4 equiv.) at 0° C., was added very slowly dropwise over a period of 0.5–1 h until no N-chloro compound could be detected by t.l.c. The resulting solution of title compound 3 was then used directly in situ in subsequent reactions. Material that was isolated by partitioning between chloroform and water and subsequent chromatography (EtOAc:petroleum ether 1:4) had Hn.m.r. (C$_6$D$_6$) δ7.49(1H, d, H-1), 4.95(1H, d, H-2 or 3), 4.54 (1H, d, H-2 or 3), 4.40(1H, br s, H-4), 3.57(2H, m, H-5,5') 1.37 and 1.26(3H each, s), 0.83(9H, s), –0.09 and –0.10(3H each, s).

Synthesis of 5-O-$^t$Butyldimethylsilyl-1-(S)-(4-chlorophenyl)-1,4-dideoxy-1,4-imino-2,3-)-isopropylidene-D-ribitol (see (6) of FIG. 11)

To a solution of 1,N-dehydro-1,4-iminoribitol 3 derived from 0.25 g of iminorbitol 4 at 78° C. was added dropwise 1.74 ml of a 2 M solution of 4-chlorophenylmagnesium bromide in dry ether. This mixture was stirred for 30 min at –78° C., allowed to warm up to r.t. and stirred for another 30 min. Ether (50 ml) and 5% aq. NH$_4$Cl (30 ml) was added and the organic layer was washed twice with water and brine, dried with MgSO$_4$ and evaporated in vacuo. Final purification by flash chromatography (petroleum ether -ethyl acetate 10:1±1% triethylamine) afforded 6 as a colourless syrup (120 mg. 0.30 mmol, 35% yield); [α]$_D^{20}$=18.0° (c=0.5 in CH$_2$Cl$_2$), HRMS calc. for C$_{20}$H$_{32}$NO$_3$Si Cl: 397.1840; found: 397.1836. $^1$Hn.m.r. (CDCl$_3$) δ 7.25 (4H, m, Ar—H), 4.40 (1H, dd, J=5.5, 7.0Hz, H-2), 4.28 (1H, dd, H-3), 4.06 (1H, d, H-1), 376, 3.66 (1H each, dd, J=10.2, and 5.5 or 3.7Hz, H-5,5'), 3.27 (1H, q, H-4), 1.49, 1.25 (3H each, s), 0.82 (9H, s), 0.08, 0.07 (3H each, s). $^{13}$C n.m.r. δ 139.8, 133.0, 128.5, 127.8, 114.1, 87.4, 81.7, 67.2, 65.4, 63.8, 27.4, 25.8, 25.3, 18.1, –5.5.

Synthesis of 5-O-'Butyldimethylsilyl-1,4-dideoxy-1-(S)-(4-fluorophenyl)-1,4-imino-2,3-O-isopropylidene-D-ribitol (7)

To a solution of 1, N-dehydro-1,4-iminoribitol 3 derived from 0.10 g of iminoribitol 4 at −78° C. was added 1.0 ml of a 2M solution of 4-fluorophenylmagnesium bromide and the reaction mixture was stirred and allowed to warm to r.t. overnight, partioned between toluene and water, filtered through celite, and the organic phase was dried (MgSO$_4$) and concentrated. Chromatography (petroleum ether, ethyl acetate 8:1) afforded title compound 7 (0.062 g, 46%). HRMS calc. for $C_{20}H_{32}FNO_3Si$: 381.2136; found: 381.2142. $^1$H n.m.r. (CDCl$_3$) δ 7.36(2H, dd, J=8.5, 5.4 Hz, Ar—H), 7.02(2H, t, J=8.6 Hz, Ar—H), 4.52(1H, dd, J=7.0, 4.6 Hz, H-3), 4.41(1H, dd, J=7.0, 5.4 Hz, H-2), 4.17(1H, d, J=5.4 Hz, H-1), 3.86 and 3.77(1H each, dd, H-5,5'), 3.36(1H, q, J=8.5, 4.6 Hz, H-4), 1.58 and 1.33(3H each, s, CH$_3$), 0.90(9H, 3, $^t$Bu), 0.08 and 0.07(3H each each, s, CH$_3$). $^{13}$C n.m.r. δ 162.2(d, $J_{C,F}$=245 Hz), 136.8(d, $J_{C,F}$=3 Hz), 128.1 (d, $J_{C,F}$=8 Hz), 115.4(d, $J_{C,F}$=8 Hz), 115.4(d, $J_{C,F}$=21 Hz), 114.3, 87.5, 81.9, 67.3, 65.5, 63.5, 27.6, 25.9, 25.4, 18.3, −5.4.

Synthesis of 1-(S)-(4-Bromophenyl)-5-O-butyldimethylsilyl-1,4-dideoxy-1,4-imino-2,3-O-isopropylidene-D-ribitol (8)

A solution of 4-bromophenyllithium [prepared by adding butyllithium (4.8 ml, 1.3 M, 6.24 mmol) slowly to 1,4-dibromobenzene (1.626g, 6.89 mmol) in tetrahydrofuran (15 ml) at 78° C.] was added via cannula to a solution of 1,N-dehydro-1,4-iminoribitol 3 derived from 0.60 g. of iminoribitol 4 at −78° C. After 1 h the reaction mixture was partitioned between chloroform and water and the organic phase was dried (MgSO$_4$) and concentrated. Chromatography (petroleum ether, ethyl acetate 8:1) afforded title compound δ (0.512 g, 55%). HRMS calc. for $C_{20}H_{32}$ $^{79}$BrNO$_3$Si; 441.1335; found, 441.1336. $^1$H n.m.r. (CDCl$_3$) δ 7.45 and 7.29(2H each, d, J=8.4 Hz, Ar—H), 4.46(1H, dd, J=4.4, 7.0 Hz, H-3), 4.35(1H, dd, J=5.3, 7.0 Hz, H-2), 4.13(1H, d, J=5.3 Hz, H-1), 3.85 and 3.73(1H each, dd, H-5, 5'), 3.35(1H, q, J=4.4, 9.8 Hz, H-4), 1.58 and 1.32(3H each, s), 0.90(9H, s), 0.08 and 0.07(3H each, s). $^{13}$C n.m.r. δ 140.7, 131.5, 128.2, 121.1, 114.1, 87.4, 81.8, 67.4, 65.5, 64.1, 27.5, 25.9, 25.4, 18.3, −5.4.

Synthesis of 1-(S)-(3-N,N-diallylaminophenyl)-5-O-'butyldimethylsilyl-1,4-dideoxy-1,4-imino-2,3-O-isopropylidene-D-ribitol (9)

To a solution of 1,N-dehydro-1,4-iminoribitol 3 derived from 0.5 g of iminorbitol 4, a solution of 3-N,N-diallylaminophenyllithium, [prepared from 3-N,N-diallylaminobromobenzene (880 mg, 3.49 mmol) in 10 ml dry ether, treated with 3.48 mmol butyllithium in hexane at −78° C. and kept at r.t. for 30 min] was added dropwise. This mixture was stirred for 30 min at −78° C., allowed to warm to r.t. and stirred for another 30 min. Ether (50 ml) and 5% aq. NH$_4$Cl (30 ml) was added and the organic layer was washed twice with water and brine, dried (MgSO$_4$) and evaporated in vacuo. Final purification by flash chromatography (petroleum ether, ethyl acetate 10:0) afforded the title compound 9 as a light yellow syrup (463 mg, 1.01 mmol, 58%); $[\alpha]_D^{20}$=−13.5° (c=2.1 in CH$_2$Cl$_2$), HRMS calc. for $C_{26}H_{42}N_2O_3Si$: 458.2964; found: 458.2978. $^1$H n.m.r. (CDCl$_3$) δ 7.08 (1H, dd, Ar—H), 6.68 (1H, s, Ar—H), 6.63 (1H, d, Ar—H), 6.52 (1H, d, Ar—H), 5.75 (2H, m, CH=), 5.08 (4H, m, =CH$_2$), 4.40 (2H, m, H-2,3), 4.04 (1H, d, J=4.0 Hz, H-1), 3.83 (4H, m, N-CH$_3$), 3.83, 3.69 (1H each, dd, H-5, 5'), 3.22 (1H, ddd, H-4), 1.49, 1.25 (3H each, s), 0.82 (9H, 3), 0.08, 0.07 (3H each, s). $^{13}$C n.m.r. δ 148.8, 142.3, 134.0, 129.2, 116.0, 114.4, 113.9, 111.4, 110.6, 87.7, 68.3, 65.7, 63.5, 52.7, 27.5, 25.9, 25.4, 18.3, −5.4.

Synthesis of 1-(S)-(4-N,N-Diallylaminophenyl)-5-O-'butyldimethylsilyl-1,4-dideoxy-1,4-imino-2,3-O-isopropylidene-D-ribitol (10)

A solution of 1,N-dehydro-1,4-iminoribitol 3 derived from 0.5 g of iminorbitol 4, was treated as described above in the preparation of 9, but using 4-N,N-diallylaminophenyllithium in place of 3-N,N-diallylaminophenyllithium. Final purification was effected by flash chromatography (petroleum ether, ethyl acetate 10:1) affording 10 as a light yellow syrup (475 mg, 1.04 mmol, 60%); $[\alpha]_D^{20}$=−17.8° (c=1.5 in CH$_2$Cl$_2$), HRMS calc. for $C_{26}H_{42}N_2O_3Si$: 458.2964; found: 458.2966. $^1$H n.m.r. (CDCl$_3$) δ 7.12 and 6.59 (2H each, d, J=8.7 Hz, Ar—H) 5.75 (2H, m, CH=), 5.08 (4H, m, =CH$_2$), 4.41 (1H, dd, J=4.8, 7.0 Hz, H-3), 4.35 (1H, dd, H-2), 4.00 (1H, d, J=5.0 Hz, H-1), 3.83 (4H, m, N—CH$_2$), 3.78, 3.68 (1H each, dd, J=10.2 Hz, H-5,5'), 3.20 (1H, q, J=4.5, 5.0 Hz H4), 1.49, 1.25 (3H each, s), 0.82 (9H, s), 0.08, 0.07 (3H each, s). $^{13}$C n.m.r. δ 148.1, 134.0, 128.9, 127.4, 116.0, 113.9, 112.5, 87.8, 81.9, 67.6, 65.7, 63.6, 52.7, 27.5, 25.9, 25.4, 18.3, −5.4.

Synthesis of 5-O-'Butyldimethylsilyl-1-(S)-(4-butyldiphenylsioxyphenyl)-1,4-dideoxy-1,4-imino-2,3-O-isopropylidene-D-ribitol (11)

A solution of 1,N-dehydro-1,4-iminoribitol 3 derived from 0.15 g of iminorbitol 4 was added via cannula at −78 ° C. to a solution of 4-'butyldiphenylsioxyphenyl lithium [prepared by adding butyl lithium (1.2 ml, 1.3 M, 1.57 mmol) slowly to a solution of O-'butyldiphenylsilyl-4-bromophenol (0.709 g, 172 mmol) in tetrahydrofuran (5 ml) at −78° C.]. After 1 h the reaction mixture was partitioned between chloroform and water and the organic phase was dried (MgSO$_4$) and concentrated. Chromatography (petroleum ether, ethyl acetate 6:1) afforded title compound 11(0.203 g, 63%). HRMS calc. for $C_{36}H_{51}NO_4Si_2$: 617.3357; found: 617.3360. $^1$H n.m.r. (CDCl$_3$) δ 7.66–7.63 (4H, m, Ar—H), 7.38–7.26(6H, m, Ar—H), 7.05 and 6.67 (2H each, d, J=8.6 Hz, Ar—H) 4.39 (1H, dd, =4.8, 7.1 Hz, H-3), 4.31 (1H, dd, J=5.2, 7.1 Hz, H-2), 3.99 (1H, d, J=5.2 Hz, H-1), 3.66 (1H each, dd, H-5,5'), 3.22(1H q, J=4.8, 8.7 Hz, H4), 1.48 and 1.25 (3H each, s), 1.03 and 0.82 (9H each, s), 0.06 and 0.05 (3H each, s). $^{13}$C n.m.r. δ 154.9, 135.5, 133.7, 133.0, 129.9, 127.8, 127.4, 119.6, 114.0, 87.5, 81.9, 67.5, 65.6, 63.7, 27.6, 26.5, 25.9, 25.4, 19.5, 18.3, −5.4.

Synthesis of 5-O-'Butyldimethylsilyl-1,4-dideoxy-1,4-imino-2,3-O-isopropylidene-1-(S)-(3-pyridyl)-D-ribitol (12)

A solution of 1,N-dehydro-1,4-iminoribitol 3 derived from 0.15 g of iminorbitol 4 was added via cannula to a solution of 3-lithiopyridine [prepared by adding butyl lithium (1.18 ml, 1.2 M, 1.4 mmol) to a solution of 3-bromopyridine (0.151 ml, 1.57 mmol) in tetrahydrofuran (3 ml) at −100° C. and subsequent stirring at this temperature for 0.5 h] at −100° C. the reaction mixture was stirred in the cold bath for 0.5 h and then partitioned between chloroform and water, and the organic phase was dried (MgSO$_4$) and concentrated. Chromatography (ethyl acetate) afforded title compound 12 (0.089 g, 46%). HRMS calc. for $C_{19}H_{32}N_2O_3$ Si: 364.2182; found: 364.2184. $^1$H n.m.r. (CDCl$_3$) δ 8.58(1H, d, Ar—H), 8.44(1H, m. Ar—H), 7.65 (1H, m, Ar—H), 7.17(1H, m, Ar—H), 4.40(1H, dd, J=4.3, 7.0 Hz, H-3), 4.33(1H, dd, J=5.3, 7.0 Hz, H-2), 4.11(1H, d, J=5.3 Hz, H-1), 3.77 and 3.65(1H each, dd, H-5,5'), 3.33–3.28(1H, m, H-4), 1.51 and 1.25(3H each, s), 0.81(9H, s), 0.08, 0.07(3H each, s). $^{13}$C n.m.r. δ 148.9, 148.5, 137.0, 134.2, 123.4, 114.2, 87.2, 81.8, 65.9, 65.6, 64.3, 27.6, 27.6, 25.9, 25.4, 18.3, −5.3.

Synthesis of 5-O-'Butyldimethylsilyl-1-(S)-(4-carboxyphenyl)-1,4dideoxy-1,4-imino-2,3-O-isopropylidene-D-ribitol (13)

Butyllithium (3.2 ml, 1.3 M, 4.16 mmol) was added dropwise to a solution of 1-(S)-4-bromophenyl)-5-O-'butyldimethylsilyl-1,4-dideoxy-1,4-imino-2,3-O-isopropylidene-D-ribitol 8 (0.385 g, 0.87 mmol) in tetrahydrofuran (10 ml) at −78° C. and the solution was stirred for 1 h at this temperature. Excess solid carbon dioxide was added and the reaction mixture was allowed to warm to room temperature. Acetic acid (2 ml) was added, the solution was partitioned between chloroform and water, the aqueous phase was extracted twice more with chloroform and the combined extracts were dried ($MgSO_4$) and concentrated. Chromatography (petroleum ether, ethyl acetate 1:1) afforded title compound 13 (0.157 g, 44%). MRMS (MH) calc for $C_{21}H_{33}NO_5Si$: 407.2128; found: 407.2138. $^1$H n.m.r. ($CDCl_3$) δ 7.94 and 7.39(2H each, d, J—8.3 Hz, Ar—H), 4.52(1H, dd, J=4.5, 6.9 Hz, H-3), 4.43(1H, t, J—6.9 Hz, H-2), 4.26(1H, d, J=5.5 Hz, H-1), 3.83 and 3.74(1H each, dd, H-5,5'), 3.42(1H, q, J=4.1,8.0 Hz, H-4),1.51 and 1.26(3H each, s), 0.81(9H, s), 0.08 and 0.07(3H each, s). 13C n.m.r. δ 170.4, 145.6, 130.4, 129.9, 126.5, 114.5, 87.2, 81.9, 67.3, 65.1, 62.9, 27.6, 25.9, 25.5, 18.3, −5.4.

Synthesis of 1-(S)-(3,N,N-diallylaminophenyl)-N-butoxycarbonyl-5-O-'butoxyldimethylsilyl-1,4-dideoxy-1,4-imino-2,3-O-isopropylidene-D-ribitol (14)

1-(S)-(3-N,N-diallylaminophenyl)-5-O-'butyldimethylsilyl-1,4-dideoxy-1,4-imino-2,3-O-isopropylidene-D-ribitol 9 (0.43 g, 0.94 mmol) was dissolved in dry dichloromethane (10 ml) and triethylamine (0.39 ml, 2.8 mmol) and di-'butyl carbonate (0.35 g, 1.6 mmol) were added at 0° C. and 3 h at room temperature. The excess of di-'butyl carbonate was hydrolysed by the addition of water and the layers were separated. The organic layer was washed twice with aqueous sodium bicarbonate, dried (MgSO4) and evaporated in vacuo. Final purification by flash chromatography (petroleum ether, ethyl acetate 10:1) afforded title compound 14 (0.525 g, 99%) as a colourless syrup: $[\alpha]_D^{20}$=−10.9° (c=0.65 in $CH_2Cl_2$), HRMS calc. for $C_{31}H_{50}N_2O_5Si$: 558.3489; found: 558.3474. $^1$H n.m.r. (DMSO-$d^6$, 90° C.) δ 7.08 (1H, dd, Ar—H), 6.55 (3H, m, Ar—H), 5.80 (2H, m, CH=), 5.11 (4H, m, $CH_2$), 4.83 (1H, m, H-3), 4.68 (1H, dd, J=1.5, 5.8 Hz, H-2), 4.59 (1H, d, J=5.8 Hz, H-1). 4.01 (1H, q, H-4), 3.87 (4H, m, N—$CH_2$), 3.73, 3.39 (1H each, dd, H-5,5'), 1.41, 1.27 (3H each, s), 1.31 (9H, s), 0.82 (9H, s), 0.08, 0.07 (3H each, s). $^{13}$C n.m. δ 155.4, 135.9, 117.3, 112.4, 87.3, 83.1, 80.6, 69.5, 67.2, 64.2, 53.9, 29.3, 28.7, 27.1, 26.8, 18.4, −4.1.

Synthesis of 1-(S)-(4-N,N-diallylaminophenyl)-N-'butoxycarbonyl-5-O-'butoxyldimethylsilyl-1,4-dideoxy-1,4-imino-2,3-O-isopropylidene-D-ribitol (15)

1-(S)-(4-N,N-Diallylaminophenyl)-5-O-'butyldimethylsilyl-1,4-dideoxy-1,4-imino-2,3-O-isopropylidene-D-ribitol 10 (0.37 g, 0.8 mmol) was treated as described above for 14. Final purification by flash chromatography (petroleum ether, ethyl acetate 10:1) afforded title compound 15 (0.45 g, 99%) as a colourless syrup. $[\alpha]_D^{20}$=−10.6° (c=2.2 in $CH_2Cl_2$), HRMS calc. for $C_{33}H_{50}N_2O_5Si$: 558.3489; found: 558.3501. $^1$H n.m.r. ($d^6$ dmso, 90° C.) δ 7.01, 6.61 (2H each, d, Ar—H), 5.80 (2H, m, CH=), 5.11 (4H, m, =$CH_2$), 4.63 (3H, m, H-1, 2, 3), 3.98 (1H, q, J=4.7, 7.5Hz, H-4), 3.87 (4H, m, N-CH2), 3.66, 3.48 (1H each, dd, J=10.2 Hz, H-5,5'), 1.41, 1.27 (3H each, s), 1.31 (9H, s), 0.82 (9H, s), 0.08, 0.07 (3H each, s). $^{13}$C n.m. δ 155.4, 148.7, 135.9, 129.5, 127.9, 117.3, 113.6, 112.4, 87.0, 82.8, 80.6, 68.5, 67.0, 64.1, 53.9, 29.3, 28.7, 27.1, 26.8, 18.4, 4.1.

Synthesis of 1-(S)-(3-Aminophenyl)-N-'butoxycarbonyl-5-O-'butyldimethylsilyl-1,4-imino-2,3-O-isopropylidene-D-ribitol (16)

1-(S)-(3-Aminophenyl)-N-butoxycarbonyl-5-O-'butyldimethylsilyl-1,4-imino-2,3-O-isopropylidene-D-ribitol 14 (0.19 g, 0.35 mmol) was dissolved in acetonitrile-:water (84:16, 40 ml). The reaction mixture was heated to vigorous boiling with a constant argon stream passed through the solution. Tristriphenylphosphine-rhodium(I) chloride (25 mg.) was added and the solvent was distilled off to a cooled (−70° C.) reservoir. The distillation, with constant replacement of the solvent mixture, was continued for 4 h until no starting material could be detected by t.l.c. (petroleum ether, ethyl acetate 1:1). The solvents were evaporated in vacuo and the residue was dissolved in ethyl acetate and filtered through silica gel. The solvent was again removed in vacuo and the crude product was finally purified by flash chromatography (petroleum ether, ethyl acetate 2:1) to afford title compound 16 (0.112 g, 66%) as a colorless syrup: $[\alpha_D]^{20}$=34.4° (c==0.55 in $CH_2Cl_2$), HRMS calc. for $C_{25}H_{42}N_2O_5Si$: 478.2863; found 478.2867. $^1$H n.m.r. (DMSO-$d^6$, 90° C.)δ6.94 (1H, dd, Ar—HO, 6.43 (3H, m, Ar—H), 4.63 (3H, m, H-1,2,3),4.03 (1H, q, J=4.7, 8.3 Hz, H-4), 3.77, 3.49 (1H each, dd, J=10.1 Hz, H-5,5), 1.41, 1.27 (3H each, s), 1.31 (9H,s), 0.82 (9H, s), 0.08, 0.07 (3H each, s), $^{13}$C n.m.r. δ155.4, 148.4, 141.7, 128.6, 113.3, 112.9, 112.4, 111.7, 86.1, 81.7, 80.6, 68.1, 65.8, 62.8, 29.3, 28.7, 27.1, 26.8, 18.4, −4.1.

Synthesis of 1-(S)-(3-Aminophenyl)-N-'butoxycarbonyl-5-O-'butyldimethylsilyl-1,4-imino-2,3-O-isopropylidene-D-ribitol (17)

1-(S)-(4-Aminophenyl)-N-butoxycarbonyl-5-O'butyldimetylislyl-1,4-dideoxy-1,4-imino-2,3-O-isopropylidene-D-ribotol 15 (0.168 g 0.3 mmol) was treated as described above for 16. Final purification by flash chromatography (petroleum ether, ethyl acetate 6:1) afforded title compound 17 (0.094 g, 63%) as a colorless syrup: $[\alpha]_D^{20}$=30.0° (c=0.85 in $CH_2Cl_2$) HRMS calc. for $C_{25}H_{42}N_2O_5Si$: 478.2863; found: 478.2854. $^1$H n.m.r. (DMSO-$d^6$, 90° C.) 6.87, 6.48 (2H each, d, Ar—H),4.65 (3H, m, H-1-2,3), 3.95(1H, q, J=4.7, 7.7, Hz, H-4) 3.67, 3.47 (1H each, dd, J=10.2Hz, H-5,5'), 1.41, 1.27 (3H each, s), 1.31 (9H, s) 0.82 (9H, s), 0.08, 0.07 (3H each, s). $^{13}$C n.m.r. δ155.4, 148.6, 129.4, 127.6, 115.1, 112.4, 87.1, 82.7, 80.6, 68.7, 67.0, 64.0, 29.3, 28.7, 27.1, 26.8, 18.4, −4.1.

Synthesis of N-'Butoxycarbonyl-5-O-'butyldimethylsilyl-1,4dideoxy-1,4imino-2,3-O-isopropylidene-1-(S)-(3-nitrophenyl)-D-ribitol (18)

1-(S)-)3-Aminophenyl)-N-'butoxycarbonyl-5-O-'butyldimethylsily-1,4-dideoxy-1,4imino-2,3-O-isopropylidene-D-ribitol 16 (0.121 g, 0.25 mmol) was dissolved in acetone (10 ml) and aq. Sodium bicarbonate solution (10 ml) was added. To this mixture a solution of oxone (0.28 g, 0.45 mmol) in water was added dropwise at 5° C. Stirring was continued for 1 h at 5° C. and 1 h at r.t. then diethylether (20 ml) was added and the layers were separated. The aqueous layer was extracted twice with diethylether and the combined organic layers were washed with water and brine, dried over $MgSO_4$ and evaporated in vacuo. Final purification by flash chromatography (petrolium ether, ethyl acetate 10:1) afforded title compound 18 (0.103 g, 80%) as white crystals, mp 93° C.; $[\alpha]_D^{20}$= −63.3° (c=0.6 in $CH_2Cl_2$), HRMS (MH$^+$) calc. for $C_{20}H_{34}N_2O_3Si$: 509.2683; found: 509.269. $^1$H n.m.r. (DMSO-$d^6$, 90° C.) δ 8.04, 8.11, 7.75, 7.64 (1Heach, Ar—H), 4.94 (1H, d, H-3), 4.69 (1H, dd, J=3.0 Hz, H-2), 4.45 (1H, d, J=5.4 Hz, H-1), 4.18 (1H, q, J+4.0, 5.3 Hz, H-4), 3.80, 3.74 (1H each, dd, J+10.5 Hz, H-5,5'), 1.41, 1.27 (3H each, s), 1.31 (9H, s), 0.82 (9H, s), 0.08, 0.07 (3H each, s). $^{13}$C n.m.r. δ 155.4, 148.2, 143.8, 132.4, 129.8, 121.8, 120.5, 112.4, 86.0, 81.5, 80.6, 68.2, 65.5, 63.1, 29.3, 28.7, 27.1, 26.8, 18.4, −4.1.

Synthesis of N-$^t$butoxycarbonyl-5-O-$^t$butyldimethylsilyl-1,4-dideoxy-1,4-imino-2,3-O-isopropylidene-D-ribitol (19)

1-(S)-(4aminophenyl)-N-$^t$butoxycarbonyl-5-O-$^t$butyldimethylsilyl-1,4-dideoxy-1,4-imino-2,3-O-isopropylidene-D-ribitol 17 (0.072 g, 0.15 mmol) was treated as described above for 18. Final purification by flash chromatography (petrolium ether, ethyl acetate 10:1) afforded title compound 19 (0.056 g, 74%) as white crystals, mp 69° C.; $[\alpha]_D^{20}$=−43.4° (c=1.0 in CH$_2$Cl$_2$), HRMS (MH$^+$) calc. for C$_{20}$H$_{34}$N$_2$O$_3$Si: 509.2683; found: 509.2672. $^1$H n.m.r.(DMSO-d$^6$, 90° C.) δ 8.17, 7.55 (2H each, d, Ar—H), 4.65 (3H, m, H-1,2,3), 4.15 (1H, q, J=4.1, 5.6 Hz, H4), 3.80, 3.73 (1H each, dd, J=10.3 Hz, H-5,5'), 1.41, 1.27 (3H each, s), 1.31 (9H, s), 0.82 (9H, s), 0.08, 0.07 (3H each, s). $^{13}$C n.m.r. δ 155.4, 149.5, 147.0, 127.1, 123.3, 112.4, 85.9, 81.5, 80.6, 68.5, 65.4, 63.0, 29.3, 28.7, 27.1, 26.8, 18.4, 4.1.

Synthesis of 1-(S)-(4-Chlorophenyl)-1,4-Dideoxy-1,4-imino-D-ribitol (20)

A solution of 5-O-$^t$butyldimethylsilyl-1-(S)-(4-chlorophenyl)-1,4-dideoxy-1,4-imino-2,3-O-isopropylidine-D-ribitol 6 (0.057 g 0.146 mmol) in 25% aqueous trifluoroacetic acid (5 ml) was stirred at room temperature for 30 mins. Water (20 ml) was added and the aqueous layer was washed twice with dichlromethane. The aqueous layer was lyophilized and the residue redissolved in water. The solution was brought to neutral pH by the addition of Amberlyst A-26 ion exchange resin (OH$^-$ form). The resin was filtered off and washed extensively with water and methanol and the solvents were evaporated in vacuo and finally removed by freeze drying to yield title compound 20 (0.028 g, 78%) an a white foam: $[\alpha_D]^{20}$=−36.2° (c=0.65 in H2O), HRMS calc for C$_{11}$H$_{14}$NO$_{3Cl}$: 243.0662 found: 243.0660. $^1$H n.m.r. (D$_2$O) δ 7.37 (4H, m, Ar—H), 3.98(3H, m, H-1,2,3), 3.70, 3.66 (1H each, dd, J=10.5 Hz, H-5,5'), 3.15 (1H, ddd, J=3.5, 5.3, 5.5 Hz, H4). $^{13}$C n.m.r. δ 140.8, 135.6, 131.5, 131.3, 79.2, 74.7, 67.4, 67.3, 64.9.

Synthesis of 1,4-Dideoxy-1-(S)-(4-Fluorophenyl)-1,4-imino-D-ribitol (21)

A solution of 5-O-$^t$butyldimethylsilyl-1,4-dideoxy-1-(S)-(4-fluorophenyl)-1,4-imino-2,3-O-isopropylidine-D-ribitol 7 (0.090 g, 0.23 mmol) in 50% aqueous trifluoroacetic acid was allowed to stand at room temperature for 3 hours and then continued to dryness. The residue was dissolved in water, washed with dicholromethane, and then the aqueous pahse was evaporated. The residue was redissolved in water and the solution was neutralized with Amberlyst A 26 ion exchange resin (OH$^-$ form), the resin was filtered off and washed liberally with methanol. The filtrate was concentrated and finally lyophilized to give title compound 21 (0.024 g, 45%). HRMS calc for C$_{11}$H$_{14}$FNO$_3$: 227.0958, found: 227.0960. $^1$H n.m.r. (D$_2$O) δ 7.44 (2H, d, J=5.5, 8.6 Hz, Ar—H), 7.17(2H, t, J=8.8 Hz, Ar—H), 4.09 (3H, br s, H-1,2,3), 3.76(2H, d, H-5,5'), 3.26(1H, q, J=5.1, 8.7 Hz, H-4). $^{13}$C n.m.r. δ 165.2 (d, Jc, f=244 Hz), 137.4, 132.1 (d, J$_{c,f}$=8.1 Hz), 118.4(d, J$_{c,f}$—21.5 Hz), 79.1, 74.8, 67.8, 67.4, 64.7.

Synthesis of 1-(S)-(4-Bromophenyl)-1,4-imino-D-ribitol (22)

1-(S)-(4-Bromophenyl)-5-O-$^t$butyldimethylsilyl-1,4-dideoxy-1,4-imino-2,3-O-isopropylidine-D-ribitol 8 (0.10 g, 0.22 mmol) was treated as described above for the preparation of 21 to give title compound 22 (0.017 G, 26%). HRMS calc for C$_{11}$H$_{14}$$^{79}$BrNO$_3$: 287.0157, found: 287.0156. $^1$H n.m.r. (D$_2$O) δ 7.58 and 7.34 (2H each, d, J=8.4 Hz, Ar—H), 4.08–3.97 (3H,m, H-1,2,3), 3.74 (2H, m, H-5, 5'), 3.19(1H, q, J=5.1, 8.9 Hz, H-4). $^{13}$C n.m.r. δ 141.7, 134.5, 132.0, 124.0, 79.4, 74.9, 67.7, 67.6, 65.1.

Synthesis of 1,4-Dideoxy-1-(S)-(4-hydroxyphenyl)-1,4-imino-D-ribitol (23)

A solution of 5-O-$^t$butyldimethylsilyl-1-(S)-(4-$^t$butyldiphenylsiloxyphenyl)-1,4-imino-2,3-O-isopropylidine-D-ribitol 11 (0.20 g, 0.32 mmole) in 50% aqueous trifluoroacetic acid (10 ml) was allowed to stand at room temperature for 16 hours and then the solution was evaporated. The residue was dissolved in water, extracted with dicholomethane (2×), and the aqueous phase was concentarted. The residue was agin dissolved in water, sirred with Amberlyst A 21 ion exchange resin (1 g) for 0.5 h, and then the solids and solvent were removed. The product was further purified by chromatography (CH$_2$Cl$_2$, MeOH 3:1) affording title compound 23 (0.061 g, 83%). HRMS (MH$^+$) calc. for C$_{11}$H$_{15}$N$_2$O$_5$: 225.1001; found 225.0999. $^1$H n.m.r. (D$_2$O) δ 7.36 and 6.95 (2H each, d, J=8.6 Hz, Ar—H), 4.34–4.18 (3H, m, H-1,2,3),3.83 (2H, d, J=5.1 Hz, H-5,5'), 3.47 (1H, q, J=4.9, 9.0 Hz, H-4). $^{13}$C n.m.r. δ 158.8, 132.1, 129.9, 118.5, 77.6, 74.1, 67.8, 67.0, 63.2.

Synthesis of 1,4-Dideoxy-1,4-imino-1-(S)-(3-pyridyl)-D-ribitol (24)

5-O-$^t$butyldimethylsilyl-1,4-dideoxy-1,4-imino-2,3-O-isopropylidine-1-(S)-(3-pyridyl)-D-ribitol 12 (0.089 g, 0.24 mmol) was treated as described in the preparation of 23 affording title compound 24 (0.031 g, 60%). HRMS (MH$^+$) calc for C$_{11}$H$_{15}$N$_2$O$_5$: 210.1002; found 210.1002. $^1$H n.m.r. (D$_2$O) δ 8.54 (1H, s, Ar—HO, 8.47 (1Hd, J+4.9 Hz, Ar—H), 7.91 (1H,d,J=8.0 Hz, Ar—H), 7.47(1H, dd, J=4.9, 8.0 Hz, Ar—H), 4.09–4.05(3H, m, H-1,2,3),3.77–3.68(2H,m,H-5, 5'), 3.25 (1H,q,J=5.4, 9.1 Hz, H-4). $^{13}$C n.m.r. δ 151.1, 150.7, 139.0, 138.8, 127.3, 79.3, 74.9, 67.8, 65.8, 65.4.

1,4Dideoxy-1,4-imino-1-(S)-(3-nitrophenyl)-D-ribitol (25)

A solution of N-$^t$butoxycarbonyl-5-O-$^t$butyldimethylsilyl-1,4-imino-2,3-O-isopropylidine-1-(S)-(3-nitrophenyl)-D-ribitol 18 (0.058 g,0.114) in methanol and 3M aqueous HCL (10 ml, 1:1) was allowed to stand at room temperature for 3 h. The methanol was removed in vacuo and the aqueous solution was washed twice with dichloromethane. The resulting solution was lyophilized and the residue was redissolved in water/methanol (5 ml, 1:1) and neutralised with Amberlyst A 26 ion exchange resin (OH form). The resin was filtered and washed extensively with water and then methanol. The solvents were evaporated in vacuo and finally lyophilized to yield title compound 25 (0.024 g, 82%) as a colourless foam: $[\alpha_D]^{20}$=−24.0° (c=0.2 in MeOH), HRMS (MH$^+$) calc for C$_{11}$H$_{15}$N$_2$O: 255.0981; found 255.0993. $^1$H n.m.r. (MeOH-d$^4$) δ 8.39, 8.26, 7.80, 7.48(1H each, Ar—H), 4.09 (1H, d, J=7.5 Hz, H-1), 3.84 (1H, m, H-3), 3.68 (1H, dd, J=5.8 Hz, H-2), 3.61 3.56(1H each, dd, J=5.0, 11.2 Hz, H-5,5'), 3.28 (1H, m, H-4). $^{13}$C n.m.r. δ 149.7, 146.0, 134.6, 130.4, 123.1, 122.8, 79.4, 73.6, 66.7, 66.5, 64.6.

Synthesis of 1,4-Dideoxy-1,4-imino-1-(S)-(4-nitrophenyl)-D-ribitol (26)

N-$^t$butoxycarbonyl-5-O-$^t$butyldimethylsilyl-1,4-imino-2,3-O-isopropylidine-1-(S)-(4-nitrophenyl)-D-ribitol 19 (0.042 g, 0.083 mmol) was treated as described above for 25 to give title compound 26 (0.015 g, 71%) as a light yellow foam: $[\alpha_D]^{20}$=−29.5° (c=0.2 in MeOH), HRMS (MH$^+$) calc for $C_{11}H_{15}N_2O$: 255.0981; found 255.0993. $^1$H n.m.r. (MeOH-d$^4$) δ 8.13, 7.64 (2H each, d, Ar—H), 4.18 (1H, d, J=7.4Hz, H-1), 3.88 (1H, dd, J=5.8, J=4.0 Hz, H-3), 3.80 (1H, dd, H-2), 3.63 (2H, AB, H-5,5'),3.22 (1H, m, H-4). $^{13}$C n.m.r. δ 151.2, 148,7, 129.3, 124.5, 79.5, 73.7, 66.8, 66.8, 64.4.

Synthesis of 1-(S)-(4-Carboxyphenyl)-1,4-dideoxy-1,4-imino-D-ribitol Ammonium Salt (27)

A solution of 5-O-$^t$butyldimethylsilyl-1-(S)-(4-carboxyphenyl)-1-4-imino-2,3-O-isopropylidine D-ribitol 13 (0.160 g, 0.39 mmol) in 50% aqueous trifluoroacetic acid was allowed to stand at room temperature for 4 hours and then concentrated to dryness. The residue, in water, was washed with dicholoromethane (2×) and then the aqueous phase was filtered and concentrated. This residue was dissolved in water and applied to a small column of Amberlyst A 15 ion exchange resin (H$^+$ form, 1.25 g). The resin was eluted with water (10 ml), which was discarded. Further elution with 2 M aqueous ammonia (20 ml) afforded, after lyophilisation, title compound 27) 0.0076 g, 71%). $^1$H n.m.r. (D$_2$O )δ 7.79 and 7.46 (2H each, d, J=7.9 Hz, Ar—H), 4.38(2H,bs), 4.20(1H, bs), 3.83(2H, bs), 3.55(1H,m). $^{13}$C n.m.r. δ 177.7, 140.4, 139.7, 132.2, 130.4, 77.6, 74.1, 68.2, 67.1, 62.9.

Synthesis of 1-(S)-(3-Aminophenyl)5-O-$^t$butyldimethylsilyl-1,4-dideoxy-1,4-imino-2,3-O-isopropylidene-D-ribitol (28)

1-(S) -(3-N,N-Diallylaminophenyl)5-O-$^t$butyldimethylsilyl-1,4-dideoxy-1,4-imino-2,3-O-isopropylidene-D-ribitol 9 (0.260 g, 0.56 mmol) was treated as described above for 16 and the crude product was purified by flash chromatography (petroleum ether, ethyl acetate 2:1) to afford pure 28 as a light yellow syrup (0.127 g, 61%). $[\alpha]_D^{20}$=−18.8° C=0.95 in CH$_2$Cl$_2$), HRMS calc. For $C_{20}H_{34}N_2O_3Si$: 378.2338; found: 378.2333. $^1$H n.m.r. (CDCl$_3$) δ 7.03, 6.68, 6.53, 6.49 (1H each, Ar—H), 4.39 (1H, dd, J=4.6, 7.0 Hz, H-3), 4.33 (1H, dd, H-2), 4.01 (1H, d, J—5.0 Hz, H-1), 3.78 (1H each, dd, J—10.2 Hz, H-5,5'), 3.22 (1H, q, J=3.7, 5.3 Hz, H-4), 1.49, 1.25 (3H each, s), 0.82 (9H, s), 0.08, 0.07 (3H each, s). $^{13}$C n.m.r. δ 146.4, 142.5, 129.7, 116.4, 113.9, 113.0, 87.4, 81.6, 67.6, 65.4, 63.5, 27.5, 25.9, 25.4, 18.3, −5.4.

Synthesis of 1-(S)-(4-Aminophenyl)5-O-$^t$butyldimethylsilyl-1,4-dideoxy-1,4-imino-2,3-O-isopropylidene-D-ribitol (29)

1-(S)-(3-N,N-Diallylaminophenyl)5-O-$^t$butyldimethylsilyl- 1,4-dideoxy-1,4-imino-2,3-O-isopropylidene-D-ribitol 10 (0.242 g. 0.52 mmol) as treated as described above for 28 to yield title compound 29 (0.131 g, 67%) as a light yellow syrup: $[\alpha]_D^{20}$=−22.0°©=0.85 in CH$_2$Cl$_2$), HRMS calc. For $C_{20}H_{34}N_2O_3Si$: 378.2338; found: 378.2330. $^1$H n.m.r. (CDCl$_3$) δ 7.09, 6.56 (2H each, d, J=8.1 Hz, Ar—H), 4.42 (1H, dd, J=4.8, 7.0Hz, H-3), 4.33 (1H, dd, H-2), 3.99 (1H, d, J=5.1 Hz, H-1), 3.78, 3.68 (1H each. Dd. J=10.2 Hz, H-5,5'), 3.21 (1H, q, J=3.6, 5.0 Hz, H-4), 1.49, 1.25 (3H each, s), 0.82 (9H,s), 0.08, 0.07 (3H each, s) $^{13}$C n.m.r. δ145.5, 131.1, 127.4, 114.9, 113.9, 87.6, 81.7, 67.4, 65.4, 27.5, 25.9, 25.4, 18.3, −5.4.

Synthesis of 1-(S)-(3-Aminophenyl)-1,4-dideozy-1,4-imino-D-ribitol (30)

1-(S)-(3-Aminophenyl)-5-O-$^t$butyldimethylsilyl-1,4-dideozy-1,4-imino-2,3-O-isopropylidene-D-ribitol 28 (0.068 g, 0.18 mmol) was treated as described above for 20 to yield title compound 30 (0.026 g, 67%) as a white foam $[\alpha_D]^{20}$=−34.9° (c=0.4 in H$_2$O). HRMS calc. for $C_{11}H_{16}N_2O_3$: 224.1160; found: 224.1161. $^1$H n.m.r.(D$_2$O) δ7.13 (1H, dd, Ar—H), 6.70 (3H, m, Ar—H), 3.92, (2H, m, H-1,3), 3.82 (1H, dd, J=3.8, J=7.5 Hz, H-2), 3.66, 3.62 (1H each, dd, J=12.5Hz, H-5,5'), 3.07 (1H, q, J=5.0 Hz, H-4). $^{13}$C n.m.r. δ149.4, 143.4, 132.6, 120.8, 118.7, 117.6, 79.3, 74.9, 68.3, 67.5, 64.7.

Synthesis of 1-(S)-(4-Aminophenyl)-1,4-dideoxy-1,4 amino-D-ribitol (31)

1-(S)-(4-Aminophenyl-5-O-$^t$butyldimethylsilyl-1,4-dideoxy-1,4-imino-2,3-O-isopropylidene-D-ribitol 29(0.107 g, 0.28 mmol) was treated as described above for 20 to yield title compound 31 (0.053 g, 84%) as a white solid with mp 166° C.$[\alpha_D]^{20}$=−44° c—0.55 in H$_2$0) HRMS calc. for $C_{11}H_{16}N_2O_3$: 224.1160; found 224.1160. $^1$H n.m.r. (D$_2$O) δ 7.21, 6.80 (2H each, d, Ar—H), 4.19 (1H, dd, J=8.5, J—5.5 Hz, H-3), 4.08 (2H m, H-1,2), 3.75 (2H AB, H-5,5'), 3.33 (1H, q, H-4). $^{13}$C n.m.r. δ149.6, 131.6, 129.5, 119.3, 77.9, 74.1, 67.7, 67.4, 63.5.

Example 9

Biological Activity of Transition State Inhibitors for N-Riboside Hydrolases and Transferases I. Materials and Methods Enzymes. Inosine-uridine nucleoside hydrolase (IU-nucleoside hydrolase) was purified from extracts of *E. coli* strain BL21 (DE3)pLysS which contained the coding region for the enzyme isolated from *C. fasciculata* in a pET3d expression plasmid. The DNA coding for the enzyme was placed in the NcoI-BamHI site. This construct gives a Pro2Ala substitution which has no significant effect on the kinetic properties of the purified enzyme. The overexpressed enzyme was purified to apparent homogeneity as previously described (Gopaul, et al. (1996) *Biochemistry* 35, 5963–5970).

The IAG-nucleoside hydrolase was purified from the blood-stream form of *T. brucei brucei* (ILTaT 1.1) grown in sublethally irradiated (650 rads) Sprague-Dawley rats. The enzyme was purified to apparent homogeneity as determined by denaturing polyacrylamide gel electrophoresis (Parkin, (1996) *J. Biol. Chem.* 271, 21713–21719). Some of the studies used the *T. brucei brucei* enzyme which was overexpressed in *E. coli*.

Enzyme Assays. Initial rate measurements were accomplished at 30° C. in reaction mixtures containing 50 mM potassium phosphate, pH 7.5, or 50 mM Hepes, pH 8.0, and nitrophenylribose or inosine as substrates (Mazella, et al. (1996) *J. Am. Chem. Soc.* 118, 2111–2112). At pH 7.5 the product p-nitrophenylate anion is present at a concentration which gives a millimolar extinction coefficient of 9.3 cm$^{-1}$ at 400 nm. Reaction mixtures with nitrophenylribose as substrate were initiated by the addition of enzyme, and product formation was monitored by continuous recording at 400 nm. With inosine as substrate, the conversion to hypoxanthine was monitored continuously at 280 nm (Parkin, et al. (1991) *J. Biol. Chem.* 266, 20658–20665). The interactions of I, V, VIII, XI, and XII (see Table V) with IU-nucleoside hydrolase were established to be slope-linear competitive inhibitors by measuring initial rates of product formation at a minimum of four substrate and three inhibitor concentrations. The remainder of the inhibitors were analyzed at one fixed substrate concentration and variable inhibitor concentrations. Inhibition constants for IAG-nucleoside hydrolase were established from full kinetic analysis with V and X as inhibitors. The results were consistent with competitive inhibition with respect to substrate. The remainder of the inhibition constants were characterized by titration of assay mixtures containing a fixed concentration of substrate with variable inhibitor concentrations. All kinetic data were fit to the equation for competitive inhibition, $v=k_{cat}A/(K_m(1+I/K_i)+A)$, where v=initial reaction rate, $k_{cat}$=catalytic turnover number, A=substrate concentration, $K_m$=Michaelis constant, I=inhibitor concentration, and $K_i$=dissociation constant for the enzyme-inhibitor complex. For $K_i$ determination at a fixed substrate concentration, this approach assumes that substrate and inhibitor compete for the catalytic site. In these cases, data were fit to the equation: $1/v=1/k_{cat}+(K_m/k_{cat}A)(1+I/K_i)$ Inhibitors. Iminoribitol inhibitor were synthesized and purified according to the methods of Furneaux, et al. (*Tetrahedron* (1997) in press), characterized by NMR, dissolved in $H_2O$ and stored at $-20°$ C. The compounds are enzymatically and chemically stable in $H_2O$ and under conditions of the assay. IU-Nucleoside hydrolase is susceptible to slow-onset tight-binding inhibition under certain conditions (Horenstein & Schramm, (1993b) *Biochemistry* 32, 9917–9925, Boutellier, et al. (1994) *Biochemistry*, 33, 3994–4000). However, in the initial reaction rate conditions described here, only the rapidly reversible competition between substrate and inhibitor is being observed. Thus, the reported kinetic constants are dissociation constants which exclude slow-onset binding.

Synthesis of 1-deoxy-1-C-phenyl-β-D-ribofuranase (XIII, Table VI) was as described by Krohn, et al. (1992) *J. Med. Chem.* 35, 511–517. The product was purified by chromatography on silica gel and characterized by NMR.

II. Results

Inhibition of IU-Nucleoside Hydrolase. The $K_m$ value for the hydrolysis of inosine by IU-nucleoside hydrolase under the conditions described here is 111±17 μM. The reaction exhibits a rapid-equilibrium random kinetic mechanism, making the $K_m$ value approximately equal to the dissociation constant (Parlin, et al. (1991) *J. Biol. Chem.* 2666, 20658–20665). For nitrophenylribose, the $K_m$ was 64±6 μM. By comparison to inosine, all of the iminoribitols, including the unsubstituted I, bind more tightly to the enzyme than does inosine (Table V). The relative affinities are conveniently expressed by the $K_m/K_i$ ratios, since these are equivalent thermodynamic constants for enzymes which follow rapid equilibrium kinetic mechanisms. The ratio ranges from 14 for II to 3960 for XII. The most tightly bound inhibitors (VI to XII) incorporate the hydrophobic phenyl ring and a group which can serve as a hydrogen-bond donor or acceptor, preferably in the para-position. The rapid equilibrium random mechanism and the intrinsic isotope effects IU-nucleosidase have established that N-ribosidic bond cleavage is the highest barrier on the reaction coordinate (Horenstein, et al. (1991) *Biochemistry* 30, 10788–10795).

Inhibition of IAG-Nucleoside Hydrolase. The $K_m$ value for IAG-nucleoside hydrolase of 18±1 μM for inosine approximates a thermodynamic dissociation constant because of the rapid-equilibrium random kinetic mechanism (Parkin, et al. (1996) *J. Biol. Chem.* 271, 21713–21719). To confirm that N-ribosidic bond cleavage is rate-limiting, the $[1'-{}^3H]$inosine kinetic isotope effect was measured for IAG-nucleoside hydrolase using the competitive isotope label method (Horenstein, et al. (1991) *Biochemistry* 30, 10788–10795). The $^3H$ kinetic isotope effect of 1.067±0.001 confirms that bond breaking occurs as part of the rate-limiting step in this reaction. Unlike IU-nucleoside hydrolase, the IAG-nucleoside hydrolase is poorly inhibited by free or substituted iminoribitols (Table V). Of the twelve compounds, in Table V, only X binds as well as the preferred substrate, inosine, as indicated by the $K_m/K_i$ ratios. The relative weak binding of these inhibitors results in $K_m/K_i$ ratios of <0.04 to 1.5.

Inhibition of Nucleoside Hydrolases by an Iminoribitol Isostere. Inhibition of the IU-nucleoside hydrolase by substituted phenyliminoribitols has been attributed to the oxocarbenium ion mimic in the iminoribitol and to combined hydrophobic and hydrogen-binding effects in the substituent (Horenstein & Schramm, (1993b) *Biochemistry* 32, 9917–9925, Horenstein & Schramm, (1993a) *Biochemistry* 32 7089–7097, Parkin & Schramm, (1995) *Biochemistry* 34, 13961–13966). These effects can be further quantitated for the IU- and IAG-nucleoside hydrolases by comparing the inhibitory action of an isostere, 1-deoxy-1-C-phenyl-β-D-ribofuranose (XIII, Table VI) to the inhibition of phenyliminoribitol (V), and to the binding of inosine as the substrate.

For IU-nucleoside hydrolase, substitution of the phenyl group in carbon-linkage to ribose in place of hypoxanthine causes a 14-fold decrease in binding affinity relative to inosine. However in the IAG-nuceloside hydrolase, the same substitution results in a decline of affinity of >1670-fold, and no binding can be detected at 10 mM of XIII. These observations indicate that Michaelis complex recognition comes primarily from the ribosyl and purine groups for the IU- and IAG-enzymes, respectively. The hydrophobic phenyl group provides some binding energy for the IU-enzyme but none for the IAG-enzyme. These observations are consistent with the more stringent purine group specificity for the IAG-enzyme.

Biochemistry. Compared to the 300 nM and 180 μM inhibition constants observed with V, the isostere XIII gives values of 1.6 and >30 for the IU- and IAG-enzymes, respectively. Relative to ribose, the presence of the iminoribitol group causes a 5300-fold increase in inhibitor affinity for IU-nucleoside hydrolase, but only a 170-fold increase for the IAG-enzyme. These findings also support the stronger preference of the iminoribitol for the IU-nucleoside hydrolase.

TABLE V

Kinetic Constants for Inhibition of Nucleoside Hydrolases by Iminoribitols.

[Structure: pyrrolidine ring with HO-CH2, N-H, R substituent, and two OH groups]

| R | IU-nucleoside hydrolase[a] $K_I$ | $K_m/K_I$ | IAG-nucleoside hydrolase[b] $K_I$ | $K_m/K_I$ | $K_m/K_I$(IU-NH) / $K_m/K_I$(IAG-NH) |
|---|---|---|---|---|---|
| (I) H | 4.5 ± 0.4 μM | 25 | 44 ± 4 μM | 0.41 | 60 |
| (II) 3-pyridyl | 7.9 ± 0.6 μM | 14 | >240[c] μM | <0.075 | >187 |
| (III) 3-nitrophenyl | 7.5 ± 0.5 μM | 15 | >360[c] μM | <0.05 | >296 |
| (IV) 4-nitrophenyl | 1.1 ± 0.1 μM | 101 | >360[c] μM | <0.05 | >2,000 |
| (V) phenyl | 300 ± 27 nM | 370 | 180 ± 15 μM | 0.1 | 3,700 |
| (VI) 4-COOH-phenyl | 96 ± 7 nM | 1,160 | >480[c] μM | <0.04 | >30,800 |
| (VII) 4-OH-phenyl | 75 ± 4 nM | 1,480 | 35 ± 2 μM | 0.51 | 2,900 |

TABLE V-continued

Kinetic Constants for Inhibition of
Nucleoside Hydrolases by Iminoribitols.

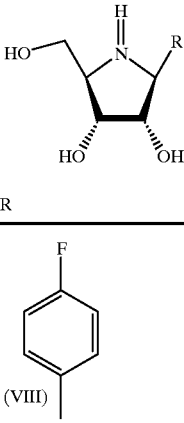

| R | IU-nucleoside hydrolase[a] | | IAG-nucleoside hydrolase[b] | | $K_m/K_I$(IU-NH) |
|---|---|---|---|---|---|
|   | $K_I$ | $K_m/K_I$ | $K_I$ | $K_m/K_I$ | $K_m/K_I$(IAG-NH) |
| (VIII) 4-F-phenyl | 57 ± 5 nM | 1,950 | 205 ± 14 μM | 0.088 | 22,180 |
| (IX) 3-NH$_2$-phenyl | 51 ± 4 nM | 2,180 | 38 ± 4 μM | 0.47 | 4,590 |
| (X) 4-NH$_2$-phenyl | 30 ± 2 nM | 3,700 | 12 ± 1 μM | 1.5 | 2,470 |
| (XI) 4-Cl-phenyl | 30 ± 1.4 nM | 3,700 | 190 ± 8 μM | 0.095 | 39,000 |
| (XII) 4-Br-phenyl | 28 ± 4 nM | 3,960 | 113 ± 5 μM | 0.16 | 24,890 |

[a]The $K_m$ for inosine was 111 ± 17 μM under these assay conditions. $K_m/K_i$ values are for inosine as substrate. Values for ! and V are from Horenstein and Schram (1993b). [b]The $K_m$ for inosine was 18 ± 1 μM under these assay conditions. $K_m/K_i$ values are for inosine as substrate. [c]NO inhibition was observed at 80, 120, 120 and 160 μM II, III, IV, and VI, respectively, when assayed at 75 μM inosine. The indicated inhibitor constants are lower limits of the constants based on the sensitivity of detecting inhibitors.

TABLE VI

Comparison of Substrate and Transition State Isosteres for Nucleoside Hydrolases.

| inhibitor | IU-nucleoside hydrolase | | IAG-nucleoside hydrolase | |
|---|---|---|---|---|
| | $K_i$ | $K_m/K_i$[a] | $K_i$ | $K_m/K_i$ |
| XIII | 600 μM | 0.07 | >30,000 μM[b] | <0.0006 |
| V | 0.30 μM[c] | 370 | 180 μM | 0.1 |

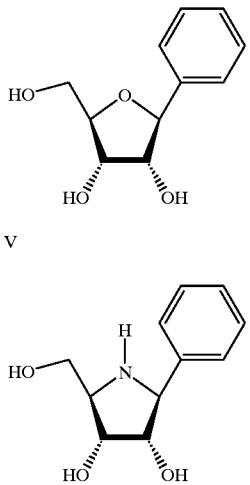

[a]The comparison is made for the inhibitors with inosine. The assays for IU-nucleoside hydrolase were in the presence of 58 μM nitrophenylriboside) using 50 mM Hepes, pH 8.0. [b]No significant inhibition was detected at 10 mM XIII using 560 μM nitrophenylriboside as substrate in 50 mM Hepes, pH 8.0. The lower limit of the $K_i$ is based on the sensitivity of the assay. [c]Taken from Horenstein and Schramm (1993b) and included for comparison.

Although the invention herein has been described with reference to particular embodiments, it is to be understood that these embodiments are merely illustrative of various aspects of the invention. Thus, it is to be understood that numerous modifications may be made in the illustrative embodiments and other arrangements may be devised without departing from the spirit and scope of the invention.

What is claimed is:

1. A compound having the formula:

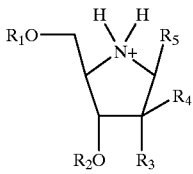

wherein R1 is hydrogen, phosphoryl, mononucleotide in phosphodiester bonding to the oxygen of R1—O, or polynucleotide in phosphodiester bonding to the oxygen of R1—O; R2 is hydrogen, phosphoryl, mononucleotide in phosphodiester bonding to the oxygen of R1—O, or polynucleotide in phosphodiester bonding to the oxygen of R1—O; R3 is hydrogen or hydroxy, R4 is hydrogen or hydroxy; and R5 is hydrogen, phenyl, pyridyl, imidazolyl, adenine, guanine, pyrimidine, or an ortho, meta or para substituted phenyl.

2. The compound of claim 1, wherein R1, R2, and R4 are hydrogen, and R3 is hydroxy.

3. The compound of claim 2, wherein R5 is hydrogen.

4. The compound of claim 2, wherein R5 is phenyl.

5. The compound of claim 2, wherein R5 is pyridyl.

6. The compound of claim 2, wherein R5 is imidazoyl.

7. The compound of claim 2, wherein R5 is nitrophenyl.

8. The compound of claim 2, wherein R5 is aminophenyl.

9. The compound of claim 2, wherein R5 is fluorophenyl.

10. The compound of claim 2, wherein R5 is chlorophenyl.

11. The compound of claim 2, wherein R5 is bromophenyl.

12. The compound of claim 2, wherein R5 is hydroxyphenyl.

13. The compound of claim 2, wherein R5 is carboxyphenyl.

14. A method for treating a subject having a parasitic infection or disease comprising administering to the subject the compound of claim 1 in an amount effective to treat the infection or disease.

15. The method of claim 14 wherein the parasitic infection or disease is selected from the group consisting of dysentary, giardiasis, vaginitis, leichmaniasis, Chagas disease, sleeping sickness, malaria, schistosomiasis, filariae disease, onchocerciosis, loiasis and infections caused by hookworm, pinworm, tapeworm and roundworm.

16. A method for treating a disease or condition caused by a toxin in a composition comprising contacting the composition with the compound of claim 1 in an amount effective to treat the disease or condition caused by the toxin.

17. The method of claim 16, wherein the toxin is selected from the group consisting of cholera toxin, diphtheria toxin, pertussis toxin, E. coli enterotoxin, Pseudomonas enterotoxin, tetanus toxin, botulinum toxin and plant toxins used in chemotherapy.

18. A pharmaceutical compostion comprising an effective amount of the compound of claim 1 with a pharmaceutically acceptable carrier, adjuvant or diluent.

19. A method for treating a composition to inactivate a parasite or toxin present therein comprising contacting the composition with the compound of claim 1 in an amount effective to inactivate the parasite or toxin.

20. The method of claim 19, wherein the toxin is selected from the group consisting of cholera toxin, diphtheria toxin, pertussis toxin, E. coli enterotoxin, Pseudomonas enterotoxin, tetanus toxin, botulinum toxin and plant toxins used in chemotherapy.

21. The method of claim 20 wherein the parasite causes a disease selected from the group consisting of dysentary, giardiasis, vaginitis, leichmaniasis, Chagas disease, sleeping sickness, malaria, schistosomiasis, filariae disease, onchocerciosis, loiasis and infections caused by hookworm, pinworm, tapeworm and roundworm.

22. The method of claim 19 wherein the composition is selected from the group consisting of blood, plasma, water and milk.

* * * * *